United States Patent
Garbey et al.

(10) Patent No.: US 10,799,146 B2
(45) Date of Patent: Oct. 13, 2020

(54) INTERACTIVE SYSTEMS AND METHODS FOR REAL-TIME LAPAROSCOPIC NAVIGATION

(71) Applicants: UNIVERSITY OF HOUSTON, Houston, TX (US); THE METHODIST HOSPITAL, Houston, TX (US)

(72) Inventors: Marc Garbey, Houston, TX (US); Brian James Dunkin, Houston, TX (US); Barbara Lee Bass, Houston, TX (US)

(73) Assignees: University of Houston System, Houston, TX (US); The Methodist Hospital, Houston, TX (US)

( * ) Notice: Subject to any disclaimer, the term of this patent is extended or adjusted under 35 U.S.C. 154(b) by 1270 days.

(21) Appl. No.: 14/667,269

(22) Filed: Mar. 24, 2015

(65) Prior Publication Data
US 2015/0265369 A1     Sep. 24, 2015

Related U.S. Application Data

(60) Provisional application No. 61/969,805, filed on Mar. 24, 2014.

(51) Int. Cl.
*A61B 5/06*     (2006.01)
*A61B 34/20*    (2016.01)
(Continued)

(52) U.S. Cl.
CPC ............ *A61B 5/061* (2013.01); *A61B 8/0833* (2013.01); *A61B 17/34* (2013.01); *A61B 34/20* (2016.02);
(Continued)

(58) Field of Classification Search
CPC . A61B 5/061; A61B 34/20; A61B 2034/2065; A61B 2034/2057;
(Continued)

(56) References Cited

U.S. PATENT DOCUMENTS 8,027,710 B1 * 9/2011 Dannan ............. A61B 1/00009
                                                    600/407
8,073,528 B2   12/2011 Zhao et al.
(Continued)

FOREIGN PATENT DOCUMENTS

WO    WO 2014/089439    6/2014

OTHER PUBLICATIONS

Hirata, Shinnosuke, et al. Accurate measurement of distance and velocity using ultrasonic waves [online]. Acoustics.org, Jun. 30, 2008 [retrieved on Dec. 11, 2018]. Retrieved from the Internet: <URL: https://acoustics.org/pressroom/httpdocs/155th/hirata.htm>.*

(Continued)

*Primary Examiner* — Patricia J Park
*Assistant Examiner* — Victoria Fang
(74) *Attorney, Agent, or Firm* — Parker Highlander PLLC

(57) ABSTRACT

Systems and methods for real time laparoscopic navigation. Exemplary embodiments can comprise scanning a structure of interest internal to a patient to provide image data; generating a first three-dimensional reconstruction of the structure of interest based on the image data; annotating the first three-dimensional reconstruction of the structure of interest with a plurality of reference points; obtaining spatial coordinates of the plurality of reference points during a laparoscopic procedure; and generating a second three-dimensional reconstruction of the structure of interest based on the spatial coordinates.

18 Claims, 15 Drawing Sheets

(51) Int. Cl.
*A61B 5/055* (2006.01)
*A61B 6/03* (2006.01)
*A61B 8/08* (2006.01)
*A61B 17/34* (2006.01)
*A61B 90/00* (2016.01)
*G03B 13/36* (2006.01)
*G06T 7/70* (2017.01)

(52) U.S. Cl.
CPC ............... *A61B 5/055* (2013.01); *A61B 5/064* (2013.01); *A61B 6/032* (2013.01); *A61B 2034/2057* (2016.02); *A61B 2034/2065* (2016.02); *A61B 2090/3937* (2016.02); *A61B 2090/3983* (2016.02); *G03B 13/36* (2013.01); *G06T 7/70* (2017.01); *G06T 2207/30056* (2013.01); *G06T 2207/30101* (2013.01)

(58) Field of Classification Search
CPC .... A61B 2090/3937; A61B 2090/3983; A61B 17/34; A61B 8/0833; A61B 5/064; A61B 5/055; A61B 6/032; A61B 2034/2055; A61B 2034/2063
USPC .................................................. 600/410, 425
See application file for complete search history.

(56) References Cited

U.S. PATENT DOCUMENTS

| | | | | |
|---|---|---|---|---|
| 8,554,307 | B2 | 10/2013 | Razzaque et al. | |
| 8,670,816 | B2 | 3/2014 | Green et al. | |
| 2005/0099824 | A1* | 5/2005 | Dowling | A61B 1/0653 362/572 |
| 2007/0034731 | A1* | 2/2007 | Falco | G01B 7/008 244/3.1 |
| 2007/0225553 | A1* | 9/2007 | Shahidi | A61B 5/064 600/103 |
| 2008/0252773 | A1* | 10/2008 | Oishi | G03B 13/32 348/347 |
| 2009/0257630 | A1* | 10/2009 | Liang | G06T 19/20 382/128 |
| 2012/0078236 | A1* | 3/2012 | Schoepp | A61B 5/061 606/1 |
| 2012/0289825 | A1* | 11/2012 | Rai | A61B 6/12 600/425 |
| 2013/0197357 | A1* | 8/2013 | Green | A61B 8/0841 600/424 |
| 2014/0037161 | A1* | 2/2014 | Rucker | A61B 5/0033 382/128 |
| 2014/0171787 | A1* | 6/2014 | Garbey | A61B 5/064 600/424 |
| 2015/0265370 | A1* | 9/2015 | Garbey | A61B 90/96 600/202 |
| 2018/0028088 | A1* | 2/2018 | Garbey | A61B 90/37 |

OTHER PUBLICATIONS

Norman, Wesley. Liver [online]. Wes Norman, Oct. 13, 2011 [retrieved on Dec. 13, 2018]. Retrieved from the Internet: <URL: https://web.archive.org/web/20111013020514/http://www.wesnorman.com/liver.htm>.*

Hayashibe, Mitsuhiro, et al. Laser-scan endoscope system for intraoperative geometry acquisition and surgical robot safety management [online]. Medical Image Analysis, 2006 [retrieved on Jul. 24, 2019], vol. 10, No. 4, pp. 509-519. Retrieved from the Internet: [URL/DOI: see office action] (Year: 2006).*

Hayashibe, Mitsuhiro, et al. Intraoperative Fast 3D Shape Recovery of Abdominal Organs in Laparoscopy [online]. Proceedings of MICCAI, LNCS, 2002 [retrieved on Jul. 24, 2019], vol. 2489, pp. 356-363. Retrieved from the Internet: [URL: see office action] [DOI: 10.1007/3-540-45787-9_45]. (Year: 2002).*

Toti, Giulia et al. A Smart Trocar for Automatic Tool Recognition in Laparoscopic Surgery [online]. Surgical Innovation, 2015 [retrieved on Jan. 6, 2020], vol. 22, No. I, pp. 77-82. Retrieved from the Internet: <URL: https://journals.sagepub. com/doi/pdf/10.1177/1553350614531659> <DOI: 10.1177/1553350614531659>.*

Kranzfelder, Michael, et al. Feasibility of opto-electronic surgical instrument identification [online]. Minimally Invasive Therapy & Allied Technologies, Sep. 15, 2009 [retrieved on May 28, 2020], vol. 18, No. 5, pp. 253-258. Retrieved from the Internet: <URL/DOI: see Office action>. (Year: 2009).*

PCT Search Report and Written Opinion issued in International Application No. PCT/US2015/022279, dated Jun. 25, 2015.

* cited by examiner

Surface Landmarks

INTERACTIVE SYSTEMS AND METHODS FOR REAL-TIME LAPAROSCOPIC NAVIGATION

CROSS-REFERENCE TO RELATED APPLICATIONS

This application claims priority to U.S. Provisional Patent Application Ser. No. 61/969,805 filed Mar. 24, 2014 and entitled "Interactive Systems and Methods for Real-Time Laparoscopic Navigation," the entire contents of which are incorporated herein by reference.

TECHNICAL FIELD

Exemplary embodiments of the present disclosure relate to systems and methods for real-time laparoscopic navigation.

BACKGROUND

Non-invasive procedures, including laparoscopic surgery, are a common and popular alternative to open surgery due to the considerable reduction of recovery time, pain and complications. However, many obstacles make the surgeon's work difficult and inefficient, including limited access to the operating field, indirect vision, and operating theaters originally built for open surgery. There has been an interest in the field to develop systems to aid in "operating room awareness." Operating room awareness refers to creating an operating room that can collect data related to the operation in progress and use the data to assist the surgeon and medical staff. There is also interest using the collected data to assist in surgeon and staff training and evaluation.

One component of operating room awareness is tool identification, location and navigation. Historically, surgical tools have been identified and positioned using visual inspection by the surgeon and/or medical staff. Some automated systems exist; however, the accuracy of these systems can be compromised by the presence of metals and fluids in the operating space and the reliance on a constantly-changing point of reference for the tracking device.

Numerous navigation systems are based on computer tomography (CT) data acquired prior to the surgery. These systems propose an accurate three-dimensional reconstruction of the liver with its Couinau decomposition into segments, blood vessel tree and tumor location. Additionally, the biliary duct network can be provided too. IRCAD (Research Institute against Digestive Cancer) has provided a data base of twenty patients that demonstrates a technique for this image analysis from CT.

This three-dimensional reconstruction can be displayed in the operating room: one uses various graphic tools to represent the structure of interest by combining rotation in the three dimensional space and transparence. As the procedure progresses, the surgeon can use a mouse or similar control device to remove virtually on that representation the tissue that has been taken away. This manually driven correction through the Graphic User Interface (GUI) may help the surgeon to visualize the next structure of interest to be reached or preserved.

This approach is quite pragmatic but loses its accuracy and relevance as soft tissue gets greatly shifted and deformed during the procedure. The surgeon has to keep connecting mentally his observation during the procedure through the endoscope camera display, to the display of the subset of preoperative data.

A technique that has potential in laparoscopy is "virtual endoscopy" or image-enhanced endoscopy. This approach uses computer graphics to render the view seen by a navigated video laparoscope inside the abdomen, based on a representation of the cavity calculated from preoperative MRI or CT images. Using segmented structures (e.g. tumor and vessels) overlaying the real laparoscopic video, is often termed augmented reality or multimodal image fusion visualization. Such a view may help the surgeons to quickly interpret important information beyond the surface of the organs as seen by the conventional video camera. More research into segmentation of anatomic and pathologic structures may improve the usefulness of e.g. overlay or side-by-side view of virtual endoscopy and tracked laparoscopic images. But the fundamental problem of shifted positions due to tissue deformation and resection remains.

Ultrasound can be used intra-operatively to follow up this displacement and replace in context the tumor location for example. In 1991, Jakimowicz and Reuers introduced Laparoscopy Ultrasound (LUS) scanning for examination of the biliary tree during laparoscopic cholecystectomy. Intraoperative ultrasound is becoming routine in some surgical disciplines, e.g. neurosurgery. LUS is today applied in laparoscopy in numerous ways for screening, diagnostics and therapeutic purposes.

Combining imaging, virtual reality and LUS could help detect organ shifts and also augment the scene view further for the surgeon, providing more details in depth and in real time.

However, manipulating the LUS probe requires additional work and may go into the way of the laparoscopic instruments. For example, the LUS probe is inserted through a trocar, which limits the ability of the probe to acquire the right view and may cause disorientation. In addition, LUS has also a lower signal to noise ratio than CT.

LUS may be useful to guide a biopsy or stage a tumor, but it is not however designed to follow continuously a surgical procedure. Finally, LUS provides a fairly limited field of view and does not help laparoscopy in that respect.

Therefore, a need in the art exists for a minimally intrusive, yet robust, system to analyze data generated during a medical procedure and provide real-time context awareness to the surgery team as well as post-procedure evaluation tools.

SUMMARY OF THE INVENTION

Presented are systems and methods directed to real-time navigation for minimally invasive procedures, including for example, laparoscopic procedures. Exemplary embodiments of the present disclosure are able to combine tissue deformation with preoperative data to produce accurately intraoperative map of a structure of interest (e.g., a liver) anatomy adapted to the real surgical procedure itself as the procedure progresses.

Exemplary embodiments of the invention may comprise: (a) a "smart" trocar and an endoscope camera, going through that smart trocar, equipped with a system that gives the distance from the lens of the endoscope camera to the tissue location centered in the endoscope camera view; and (b) a simulator of tissue deformation that starts from preoperative imaging data.

Exemplary embodiments may use the elements described in (a) and (b) above to compute at any time of the surgery, and on-demand, the three-dimensional map of the tissue in the region of interest. In exemplary embodiments, this map can to help the surgeon to navigate through this anatomy and achieve exact resection as planned. Embodiments of the system are designed to make surgery safer, e.g. by avoiding damage to tissue that should not be cut during the surgery.

Certain embodiments include a method of scanning a structure of interest internal to a patient to provide image data, and generating a first three-dimensional reconstruction of the structure of interest based on the image data. Exemplary methods can also include annotating the first three-dimensional reconstruction of the structure of interest with a plurality of reference points, and obtaining spatial coordinates of the plurality of reference points during a laparoscopic procedure. Exemplary methods may further comprise generating a second three-dimensional reconstruction of the structure of interest based on the spatial coordinates.

In particular embodiments, obtaining the spatial coordinates of the plurality of reference points comprises obtaining a distance from each of the plurality of reference points to a camera on a surgical port used during the laparoscopic procedure. In some embodiments, the distance is obtained via a laser. In specific embodiments, the distance is obtained via acoustic waves. In certain embodiments, the distance is obtained via an autofocus feature of the camera. In particular embodiments, the autofocus feature incorporates an algorithm to increase local pixel contrast. In specific embodiments, the structure of interest is a liver. In some embodiments, the plurality of reference points comprise locations where hepatic arteries enter the liver and where a portal vein exits the liver. In particular embodiments, the plurality of reference points comprise locations including a transverse fissure of the liver that divides a left portion of the liver into four segments. In certain embodiments, the plurality of reference points comprises a coupling point between the liver and a gall bladder. In particular embodiments, the plurality of reference points comprises a location of the hepatic lymph node. In some embodiments, the plurality of reference points comprise the ligamentum venosum and the ligament teres.

Certain embodiments include a real time laparoscopic navigation system comprising a scanner configured to provide image data of a structure of interest internal to a patient, and a processor. In particular embodiments, the processor is configured to: generate a first three-dimensional reconstruction of the structure of interest based on the image data; annotate the first three-dimensional reconstruction of the structure of interest with a plurality of reference points; obtain spatial coordinates of the plurality of reference points during a laparoscopic procedure; and generate a second three-dimensional reconstruction of the structure of interest based on the spatial coordinates. In certain embodiments, the scanner is a magnetic resonance imaging (MRI) scanner. In some embodiments, the scanner is a computed tomography (CT) scanner.

Specific embodiments further comprise a camera coupled to a surgical port, and wherein the processor is configured to obtain the spatial coordinates of the plurality of reference points by obtaining a distance from each of the plurality of reference points to the camera. In particular embodiments, the processor is configured to obtain the distance via a laser. In some embodiments, the processor is configured to obtain the distance via acoustic waves. In specific embodiments, the processor is configured to obtain the distance via an autofocus feature of the camera. In particular embodiments, the autofocus feature incorporates an algorithm to increase local pixel contrast.

Certain embodiments can comprise a scanner (e.g. a magnetic resonance imaging [MRI] scanner or a computer tomography [CT] scanner) to scan the structure of interest. Exemplary embodiments may also comprise one or more processors and graphic displays to analyze the image data and generate reconstructions of the structure of interest.

Exemplary embodiments of the present disclosure extract spatially and timely accurate data from the minimally invasive procedures. In certain embodiments, the system can be passive in the sense that it can provide feedback, but the surgical team has still the ability to ignore or override the outcome. In certain embodiments, it may be desirable to implement the system in a passive manner to allow the surgical team to become familiar and comfortable using the system.

In other embodiments, the system may be operated in an active manner (e.g. after the surgeon team has become familiar the operation of the system in a passive aspect). In such embodiments, the system can be configured to restrict or stop the procedure when it determines the surgical instrument has entered a restricted area (e.g. a "no-fly zone") that could place critical structures in danger.

Challenges faced in such systems and methods include the difficulty in tracking landmarks that can be acquired in a non invasive way. Exemplary embodiments of the present disclosure utilize a global positioning system to provide the location of the surgical port used during the laparoscopic procedure, as well as image data from the structure of interest to address such challenges.

Exemplary embodiments of the system can also include a surgical port, and one or more reference markers and tracking elements associated with a surgical tool and a camera. The surgical port may have a proximal end configured to be located outside the body of a patient and a distal end configured to be located within an internal portion of the body of the patient. The surgical port may also have a channel extending between the proximal end and the distal end. The surgical tool may be sized and configured to access the internal portion of the body of the patient through the channel of the surgical port. The reference markers may be located distal to the camera, and the tracking elements may be removably coupled to the surgical tool and a camera mounted to the proximal end of the surgical port may be configured to capture image data associated with the tracking element.

Another aspect of the present disclosure is directed to a method of tracking a surgical tool. The method may include providing a surgical tool to a surgical port where the surgical tool may include a tracking element and the surgical port may include a camera mounted thereto. The method may further include capturing image data at the camera. The method may further include providing the image data to a processor and determining, at the processor, tracking information associated with the surgical tool.

A further aspect of the present disclosure is directed to an information management system for managing medical procedure information. The system may receive image data from a camera associated with a surgical port, the image data representative of a reference marker and/or a tracking element associated with a surgical tool. The image data is not associated with a particular finite set of known tools. The system may further determine an identity and a location of the surgical tool based on the image data. The system may also determine a surgical step of a medical procedure using the image data and determine procedure management information by comparing the image data associated with the surgical step with the medical procedure.

The details of one or more embodiments of the invention are set forth in the accompanying drawings and the description below.

Certain terminology is used in the following description are for convenience only and is not limiting. The words "right", "left", "lower", and "upper" designate direction in the drawings to which reference is made. The words "inner", "outer" refer to directions toward and away from, respectively, the geometric center of the described feature or device. The words "distal" and "proximal" refer to directions taken in context of the item described and, with regard to the instruments herein described, are typically based on the perspective of the surgeon using such instruments. The words "anterior", "posterior", "superior", "inferior", "medial", "lateral", and related words and/or phrases designate preferred positions and orientation in the human body to which reference is made. The terminology includes the above-listed words, derivatives thereof, and words of similar import.

In the following, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The terms "about", "approximately" or "substantially" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

BRIEF DESCRIPTION OF THE DRAWINGS

Exemplary embodiments of the present disclosure are provided in the following drawings. The drawings are merely examples to illustrate the structure of exemplary devices and certain features that may be used singularly or in combination with other features. The invention should not be limited to the examples shown.

DETAILED DESCRIPTION

Figure 1:
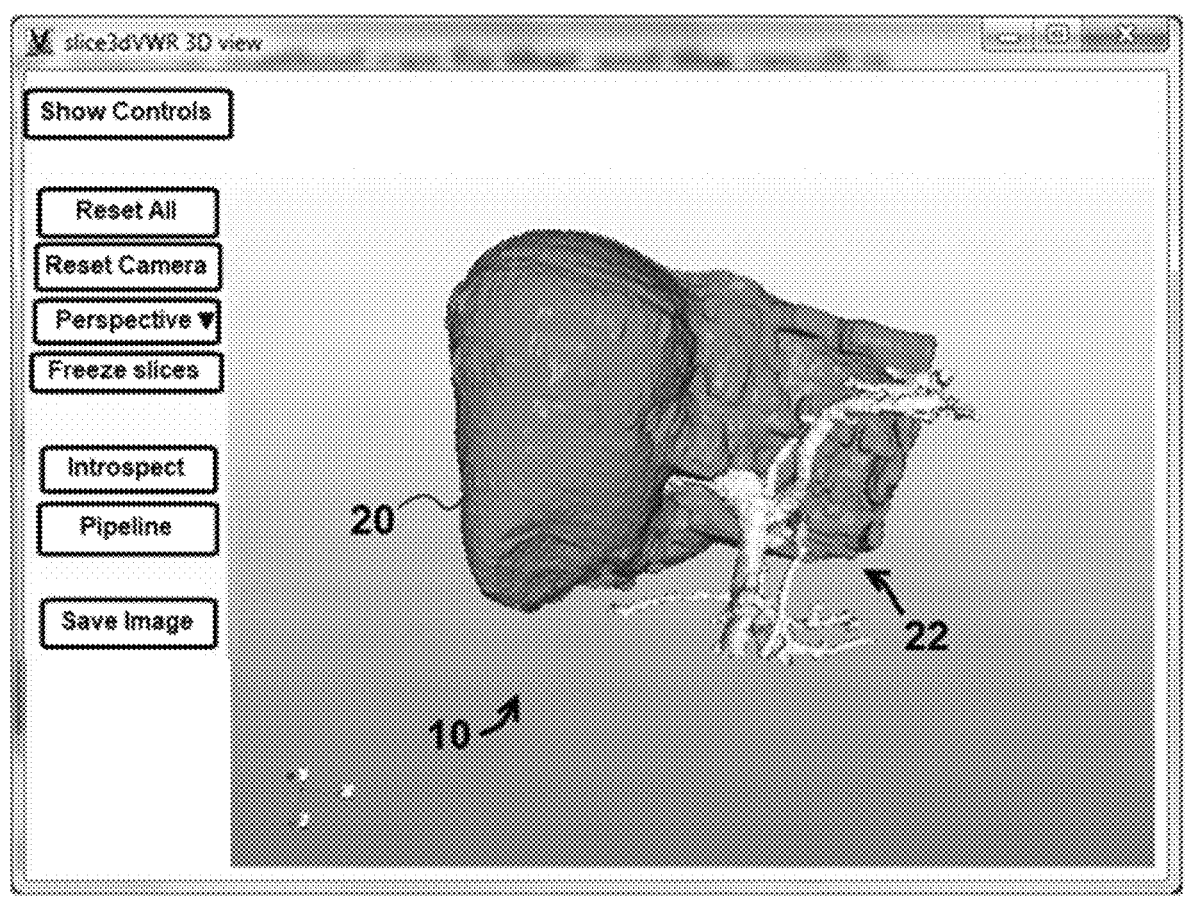
FIGS. 1-2 illustrate an initial three-dimensional image reconstruction of a structure of interest.
Figure 2:
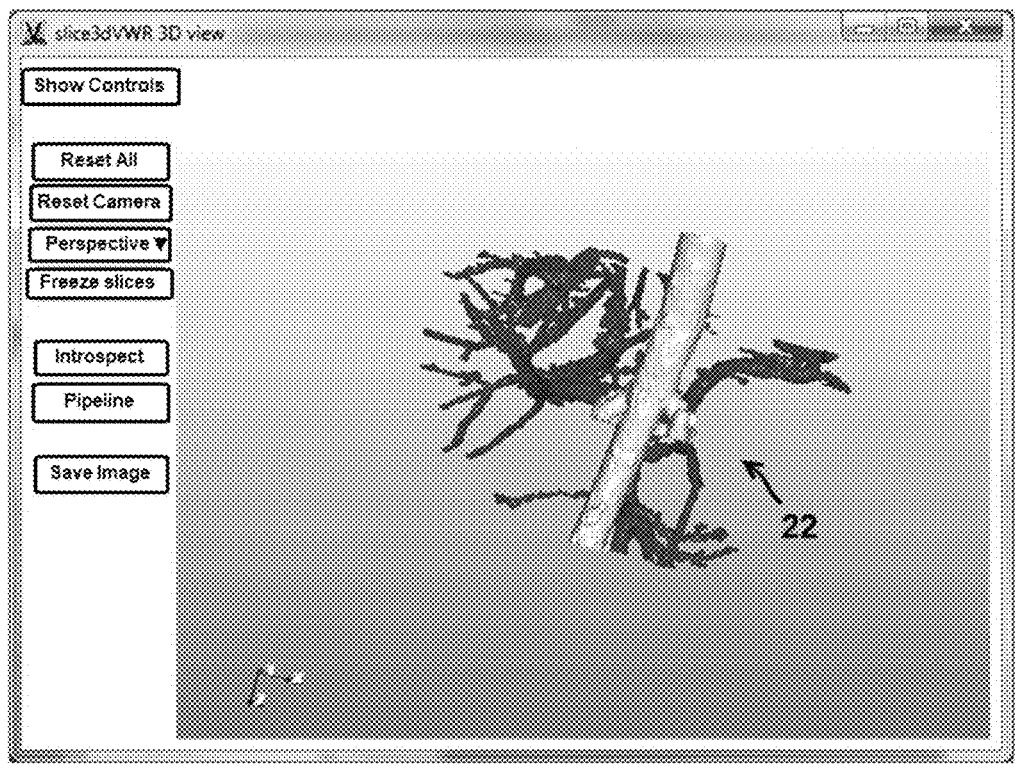

Referring now to FIGS. 1-2, an initial three-dimensional image reconstruction 10 of a structure of interest 20 (e.g. a liver in this embodiment) is generated from image data obtained from a preoperative scan. In certain embodiments, the image data may be obtained via a computed tomography (CT) scanner, while in other embodiments the image data may be obtained from a magnetic resonance imaging (MRI) scanner. While a liver is shown as structure of interest 20 in this embodiment, it is understood that other embodiments may be directed to other anatomical structures.

Figure 3:
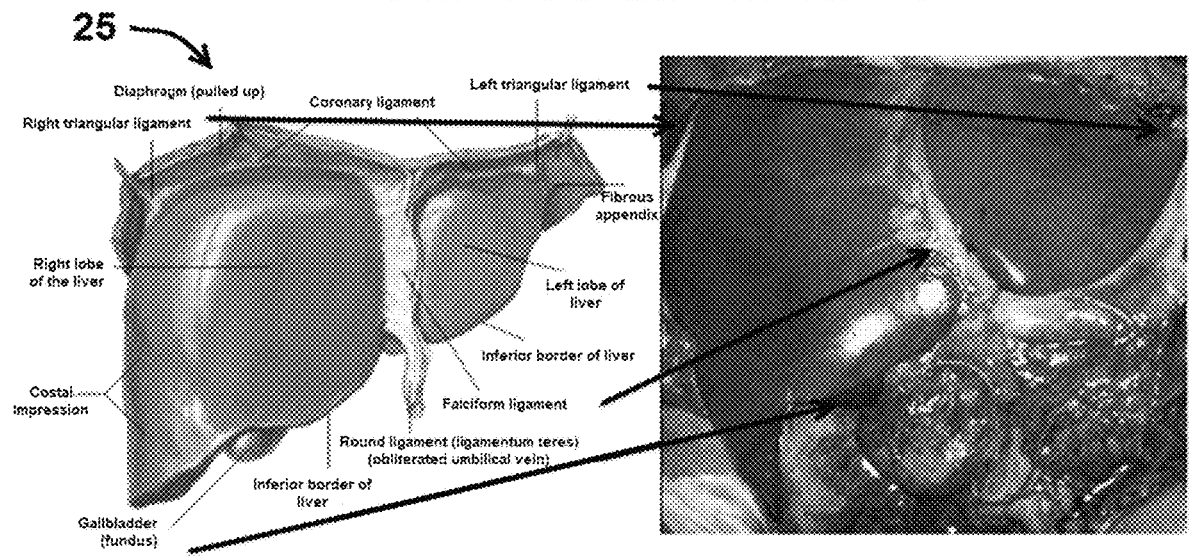
FIGS. 3-4 illustrate an image reconstruction annotated with landmarks or reference points.
Figure 4:
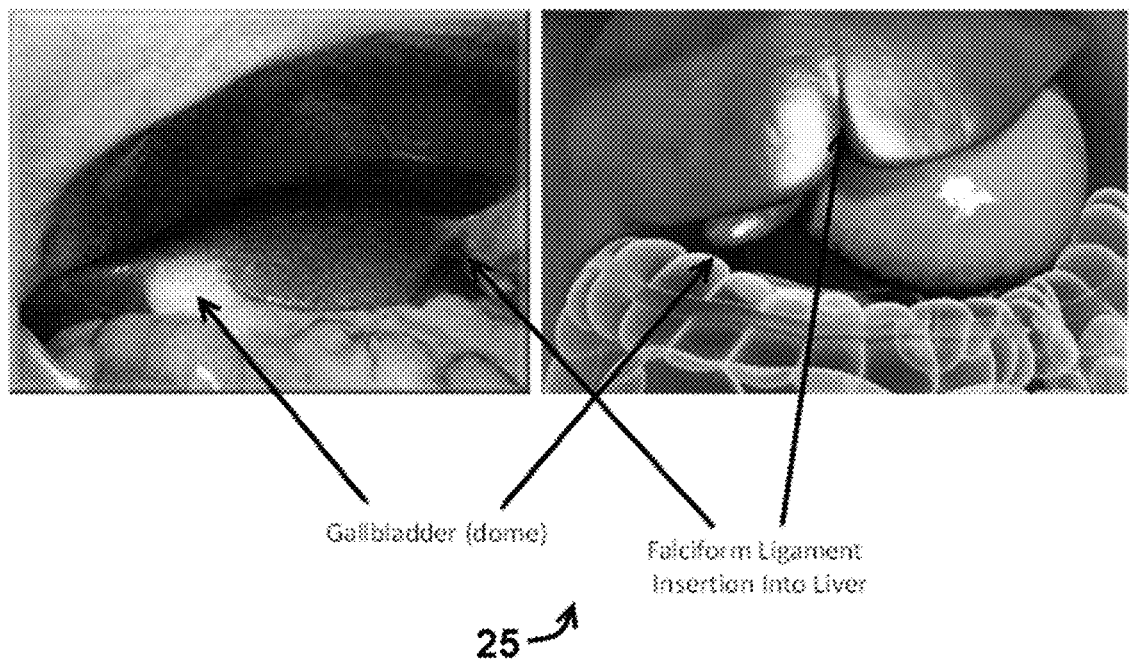

As shown in the figures, initial three-dimensional image reconstruction 10 includes representations 22 of the Couinaud system, arteries, venous and hepatic ductal structures of structure of interest 20. As shown in FIGS. 3 and 4, image reconstruction 10 can be annotated with landmarks or reference points 25 that will be encountered during the planned laparoscopic procedure. In certain embodiments, reference points 25 can include the locations where hepatic arteries enter the liver and portal vein exit the liver, as well as the transverse fissure of the liver which divides the left portion of the liver into four segments. Other exemplary embodiments may include reference points 25 such as gall bladder attachment location and the location of the hepatic lymph node. As shown in FIG. 4, still other reference points 25 may include, for example, the location where the falciform ligament which attaches the liver to the posterior portion of the anterior body wall, as well as the locations of the ligamentum venosum (ligamentum of Arancio) and the round ligament (ligamentum Teres). The foregoing list of reference points is merely exemplary, and other embodiments may comprise different reference points than those listed here.

Figure 5:
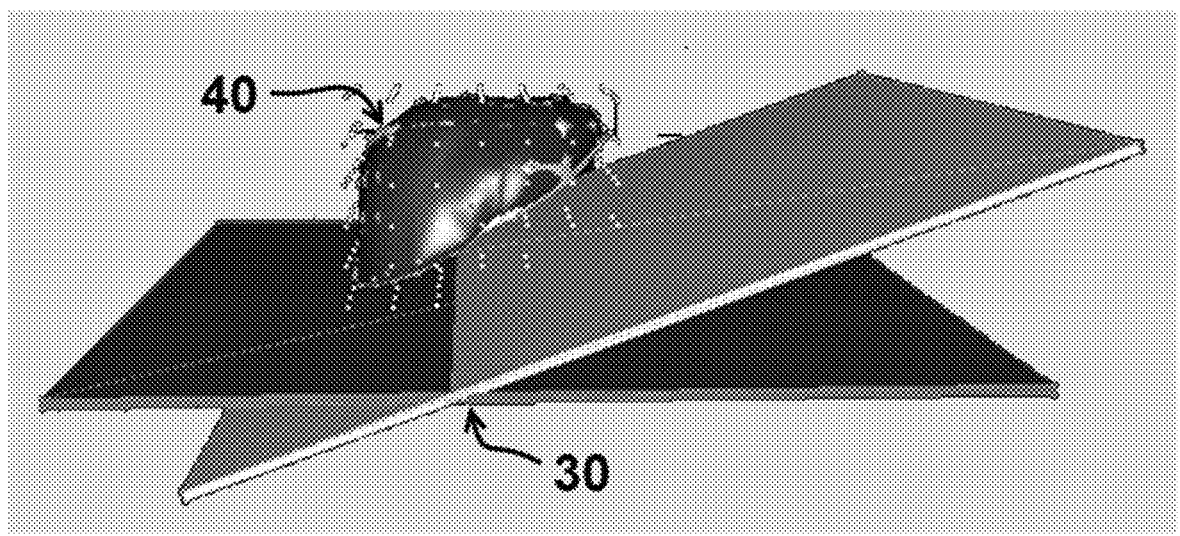
FIGS. 5-6 a tissue deformation simulation is illustrated for a structure of interest.
Figure 6:
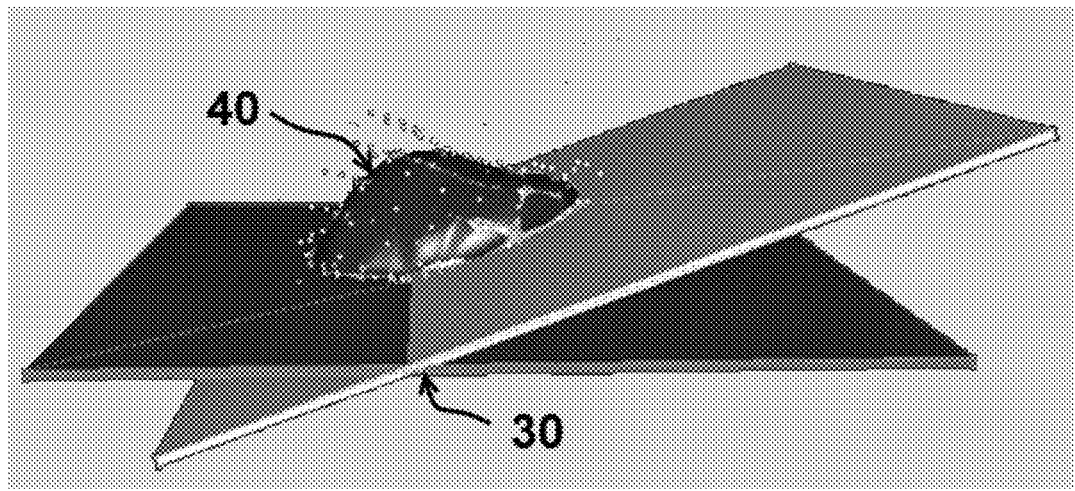

Referring now to FIG. 5-6, a tissue deformation simulation is illustrated for a structure of interest 40 (e.g. a liver) from zero gravity to standard gravity with a support surface 30 comprising two articulated plates. The figures illustrate a simulation set up of the tissue mechanical deformation module, with an initial shape for structure of interest 40 shown in FIG. 5. The tissue deformation simulation for structure of interest 40 is shown in FIG. 6. Such a deformation can be used to simulate the changes in the shape of the structure of interest that may be encountered during a non-invasive procedure such as a laparoscopic surgery. Such procedures can make it difficult for the surgeon to visualize the shape of the structure of interest due to limited visual access. In exemplary embodiments, the simulation of the structure deformation can be established with boundary conditions that match the three-dimensional reconstruction from preoperative computer tomography data.

Figure 7:
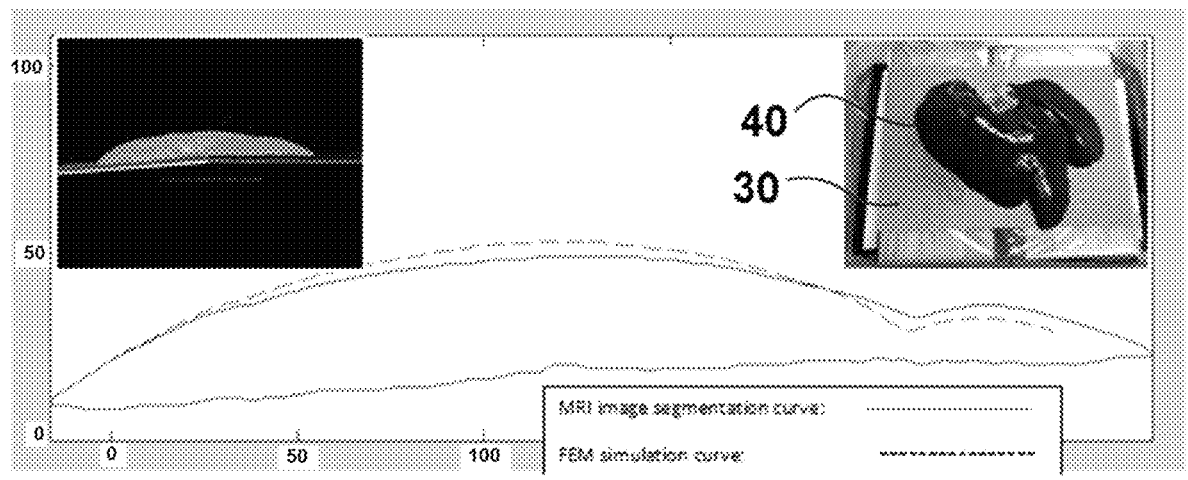
FIG. 7 is a validation of a tissue deformation model for a structure of interest.

Referring now to FIG. 7, a validation of a tissue deformation model is illustrated utilizing a pig liver as structure of interest 40. The upper right portion of the figure shows structure of interest 40 on support surface 30 with two articulated plates. The solid line in FIG. 7 illustrates the tissue surface of structure of interest 40 before articulation of support surface 30, and tissue surface deformation as recorded in a magnetic resonance imaging (MRI). The dashed line in FIG. 7 illustrates the tissue deformation of structure of interest 40 after articulation of support surface 30 as modeled with a linear elastic model (LEM). Although the LEM utilized to generate the data shown in FIG. 7 can be computed in real-time, exemplary embodiments can utilize a hyper elastic model along with a reduction method. Such features can be implemented to combine accuracy and computational speed improvements in real-time accuracy.

Exemplary embodiments of the present disclosure can rely on a real-time navigation system that utilizes the image base simulation of the structure of interest deformation. Exemplary methods may comprise scanning a structure of interest to provide image data and generating a first three-dimensional reconstruction of the structure of interest based on the image data. Exemplary methods can also comprise annotating the first three-dimensional reconstruction of the structure of interest with a plurality of reference points, and obtaining spatial coordinates of the plurality of reference points during a laparoscopic procedure. Furthermore, methods may comprise generating a second three-dimensional reconstruction of the structure of interest based on the spatial coordinates.

Figure 8:
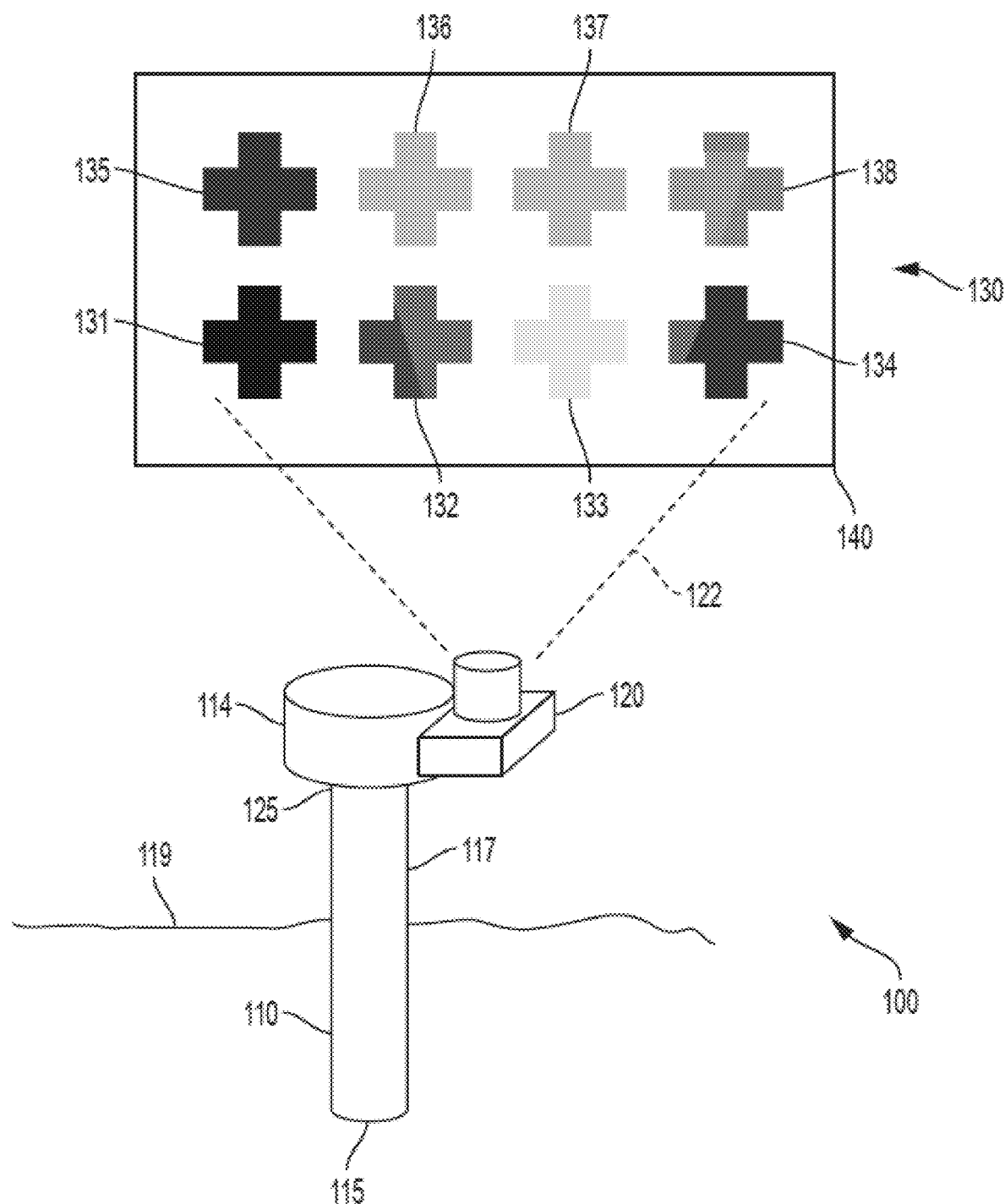
FIG. 8 is a schematic view of an example system configured for surgical tool global positioning.
Figure 9:
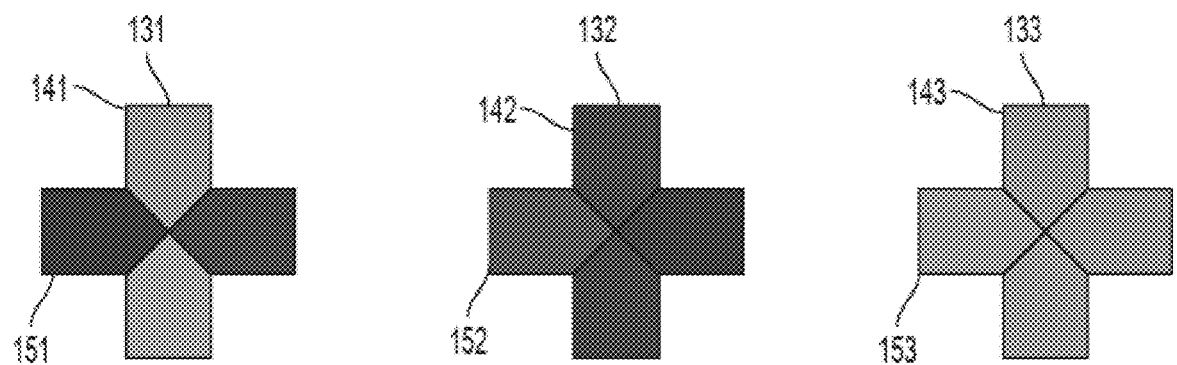
FIG. 9 is view of example reference markers of the system of FIG. 8.

Referring now to FIGS. 8-9, a system 100 configured for surgical tool global positioning is displayed. As explained in further detail below, system 100 can be used to obtain position data for system components (e.g. a surgical tool or a camera coupled to a surgical port). The position data of the system components can be used to assist in obtaining spatial coordinates for reference points of the structure of interest.

In the embodiment shown, system 100 comprises a surgical port 110 comprising a proximal end 125 configured to be located outside a body of a patient 119 and a distal end 115 configured to be located within an internal portion of the body of patient 119. In the illustrated embodiment, surgical port 110 comprises a channel 117 extending between proximal end 125 and distal end 115.

In the embodiment of FIGS. 8-9, system 100 further comprises a plurality of reference markers 130 positioned at a first fixed location 140 distal to surgical port 110. In the embodiment shown, the plurality of reference markers 130 comprises individual reference markers 131-138. In particular embodiments, fixed location 140 may be positioned on the ceiling of a room in which surgical port 110 is located, including for example, a ceiling of an operating room.

In addition, the embodiment of system 100 shown comprises a camera 120 coupled to proximal end 125 of surgical port 110. In this embodiment, camera 120 comprises a field of view 122 configured to capture image data associated with one or more reference markers 131-138. As shown in FIG. 9, reference marker 131 may comprise a first segment 141 intersecting with a second segment 151 to form a cross shape. Similarly, reference marker 132 comprises intersecting segments 142 and 152, while reference marker 133 comprises intersecting segments 143 and 153. The remaining reference markers 134-138 can be similarly constructed. It is understood that the geometry, arrangement and number of reference markers shown is merely one example of several different configurations possible in embodiments of the present disclosure.

As explained in more detail below, image data associated with one or more reference markers 131-138 may be used to determine a global position of surgical port 110, as well as a tool inserted into surgical port 110. Certain embodiments can utilize camera 120 in a manner similar to a "virtual optical pointer" to get accurate spatial coordinate of landmarks as they appear in the procedure. For each new set of landmarks that has been selected, system 100 can compute on demand (e.g. via a processor) the new three-dimensional map of the structure of interest that matches the landmark and visualizes the internal structure of interest.

With a new coordinate system, camera 120 can be used as a pointer to let system 100 register where the cut or resection should occur for the structure of interest. In exemplary embodiments, camera 120 can be directed toward a landmark, similar to how one would use a laser pointer in a presentation. Camera 120 may not include the capability of providing accurate three-dimensional spatial coordinates. However, surgical port 110 can provide the three-dimensional spatial coordinates of the camera 120 and its orthogonal optical axis (as explained in the discussion of FIGS. 8-9).

The distance from the camera 120 to the point of interest along that axis on the surface of a structure of interest needs to be computed in order to complete the registration. There are multiple ways of providing such information. For example, a hardware solution may comprise laser measurement or acoustic wave measurement. Furthermore, a software solution may be implemented using a passive autofocus technique that for example increases the local pixel contrast, or any similar algorithmic technique to get the depth map. Still other embodiments may utilize a hybrid solution by projecting two light spots from some fixed optical fibers coupled to the surgical port 110, and using the known view angle of the endoscope camera to give this distance accurately.

In certain exemplary embodiments, the number of constraints in the tissue mechanical problem set up from landmark identifications should be larger than needed to provide redundancy. If matching the structure of interest position to the landmark generates too much local mechanical stress in the simulation, the system can interpret that result as a fault, and may require new recalibration of the landmark to the operator.

Once the structure of interest position has been recalculated, one can use the surgical port 110 to tentatively show the location of a planned resection: the system may then compute estimates of the margin to structure such as vessel that should be preserved, or volume of the tissue that will be removed or even negative margin for tumor removal. In exemplary embodiments, the plan for cut can be set in the new coordinate system at that step of the intervention with the updated position of the structure of interest.

It is anticipated that exemplary embodiments can be even more powerful if used with existing methods that are not fully satisfactory as standalone solution. For example, pattern recognition on the structure of interest surface image of the endoscope is not a robust method by itself. However, the same method combined with landmark annotation according to exemplary embodiments would perform better since it becomes a local optimization mathematical problem as opposed to a global mathematical one that has to deal with many local optimums. Laparoscopic ultrasound (LUS) also provides local information on localization that complements registration techniques based on spatially distributed landmarks according to exemplary embodiments. LUS that comes with elastography measurements can also improve image base tissue deformation models by providing more accurate tissue properties to feed the mechanical model.

Systems and methods to provide global position and orientation coordinates will be described in the discussion of FIGS. 8-22. As previously mentioned, image data associated with one or more reference markers 131-138 may be used to determine a global position of surgical port 110, as well as a tool inserted into surgical port 110.

Figure 10:
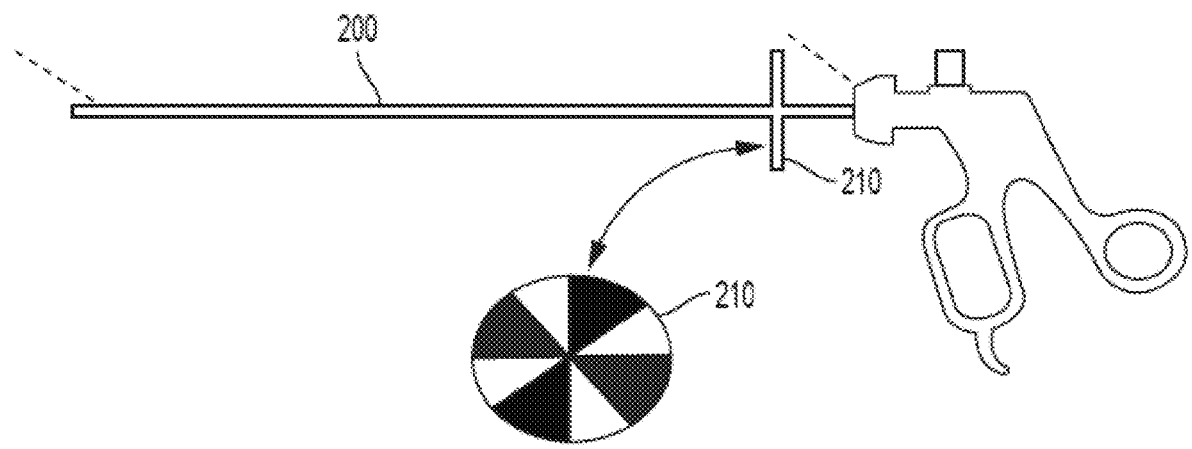
FIG. 10 is a schematic diagram of an example tool configured for use with the system of FIG. 8.

Referring now to FIG. 10, a tool 200 is configured for insertion into surgical port 110 (shown in FIG. 8). In this embodiment, a tracking element 210 is coupled to surgical tool 200. As shown in FIG. 10, tracking element 210 is circular in shape and includes a pattern of geometric shapes on one side (e.g. segments of a circle in this embodiment). During use, tool 200 may be inserted into surgical port 110 such that the circular shape and pattern of tracking element 210 can be detected by camera 120. In certain embodiments, tracking element 210 may be configured similar or equivalent to the tool identification marker as disclosed in U.S. patent Ser. No. 14/099,430, incorporated by reference herein. Particular embodiments may also comprise separate cameras for detecting image data associated with tracking element 210 and reference markers 131-138.

In exemplary embodiments, surgical port 110 can be placed into an incision in the body of patient 119 and provide an access point through which surgical instruments may be introduced into an internal surgical site. In certain embodiments, surgical port 110 can include a needle, a cannula, a trocar, or any other style of surgical port known in the art. Surgical port 110 can be composed of a biocompatible material. It is contemplated that the surgical port 110 can be constructed from a disposable material thereby reducing cost and avoiding problems of sterilization and battery change. Surgical port 110 can have a proximal end 125 configured for location on the outside of the patient's body and a distal end 115 sized and configured to extend into the internal portion of the patient's body. Channel 117 can extend through surgical port 110 to provide access to an internal portion of the patient's body such that a surgical tool 200 (e.g. a laparoscope, endoscope or other tool as shown in FIG. 10), can be inserted into the patient's body via channel 117.

Exemplary embodiments of surgical tool tracking system 100 can include a camera 120 mounted to proximal end 125 of surgical port 110. Camera 120 can capture visible spectrum and/or infra-red light or include any other imaging modality suitable for use with surgical procedures. Camera 120 can be configured to capture and store video and/or still images. Camera 120 may also be configured to capture and store audio data. Camera 120 can be configured to capture image data associated with reference markers 130 and tracking element 210 including still and/or video images. Camera 120 may be further configured to capture image data associated with a surgeon performing the medical procedure. For example, camera 120 can capture image data providing surgeon-identifying information such as a surgeon-specific tracking element or marker. An example surgeon-specific marker can include a particular colored glove worn during the medical procedure. The image data associated with the surgeon can also include motion information with respect to surgical tool 106 and/or the surgeon's hand. The motion information can be used to track the motion/path of the surgeon's hands and/or surgical tool 106 during the medical procedure.

In certain exemplary embodiments, camera 120 can be coupled to surgical port 110 via mounting to base 114 of proximal end 125. In other exemplary embodiments, camera 120 can be incorporated with or otherwise integral to base 114. The location of camera 120 with respect to the surgical port 110 can be fixed such that camera 120 can be mounted to or otherwise incorporated into the base 114 at a fixed and set position. In other embodiments, the location of camera 120 can be changed or adjusted with respect to surgical port 110. For example, camera 120 can be mounted to base 114 using an adaptor that controls the position and orientation of camera 120.

In certain embodiments, camera 120 can be mounted to the base 114 such that the optical lens/field of view of camera 120 is directed away from the body of the patient. For example, camera 120 can be mounted to the base 114 such that the optical lens/field of view of camera 120 is provided in a direction of reference markers 131-138, tracking element 210 and/or the surgeon's hand as surgical tool 200 approaches and/or is inserted into surgical port 110. In a further example, camera 120 can be mounted to base 114 such that the optical lens/field of view of camera 120 is both directed away from the body of the patient and in a direction of reference markers 131-138, tracking element 210 and/or the surgeon's hand as surgical tool 200 approaches and/or is inserted into surgical port 110. For example, it is contemplated that the optical lens/field of view of camera 120 can be configured to capture image data of reference markers 131-138, tracking element 210 and/or surgeon's hand as surgical tool 106 approaches and is located within surgical port 110.

In particular embodiments, camera 120 can include a light element for illuminating reference markers 131-138, tracking element 210 and/or the surgeon. For example, light element can include an ultraviolet LED that illuminates a UV sensitive feature on reference markers 131-138 and/or tracking element 210. The use of a non-visible light range should not disturb a surgeon preferring to operate in low light conditions. Use of the a UV sensitive feature on reference markers 131-138 and/or tracking element 210 can also have positive effects on the recognition process because reference markers 131-138 and tracking element 210 will appear to the system a bright and colorful item in the image, thus making it more distinguishable from the background and/or image noise.

In certain embodiments, camera 120 may be capable of operating on a wired or wireless communication network. Camera 120 may be configured to communicate with other devices using the communication network, the other devices including computers, personal data assistants (PDAs), mobile telephones, and mobile computers. For example, tracking system 100 can include a computer system (not shown). Camera 120 can be in communication with the computer system to transmit image data to the computer system for analysis and/or storage. Tracking system 100 may include other components capable of acquiring, storing, and/or processing any form or type of data. Any such component may be coupled to or integrated into base 114 or may be communicatively coupled to tracking system 100 and/or the computer system.

As explained in further detail below, image data obtained by camera 120 and associated with reference markers 131-138 can be used to calculate a global position of laparoscopic tool 200. In the mathematical equations presented herein, it is assumed that the geometry and shape of laparoscopic tool 200 with precise measurement is known. In principle, this information can be provided by the vendor for tool 200. It is also assumed tracking element 210 has a rigid attachment to the tool and is perpendicular to the axis of the tool. The location of the tracking element 210 on the axis is known as shown in FIG. 10.

The motion of laparoscopic tool 200 is channeled by surgical port 110. The motion can be decomposed into: (a) a translation along the main axis of surgical port 110; and (b) a small deviation from the port axis allowed by the difference in diameters between surgical port 110 and tool 200.

The position of the tool 200 in a coordinate system coupled to surgical port 110 can then be determined. If the axis of tool 200 is perfectly aligned to the axis of surgical port 110, the distance from tracking element 210 to surgical port 110 can be computed from the apparent diameter of tracking element 210 in the image data (e.g. video stream). If the port and tool axes are not aligned, tracking element 210 will appear as an ellipse, instead of a circle, in the image data. The axis of the ellipse small diameter and the axis of laparoscopic tool 210 can provide the plan of the rotation.

Figure 11:
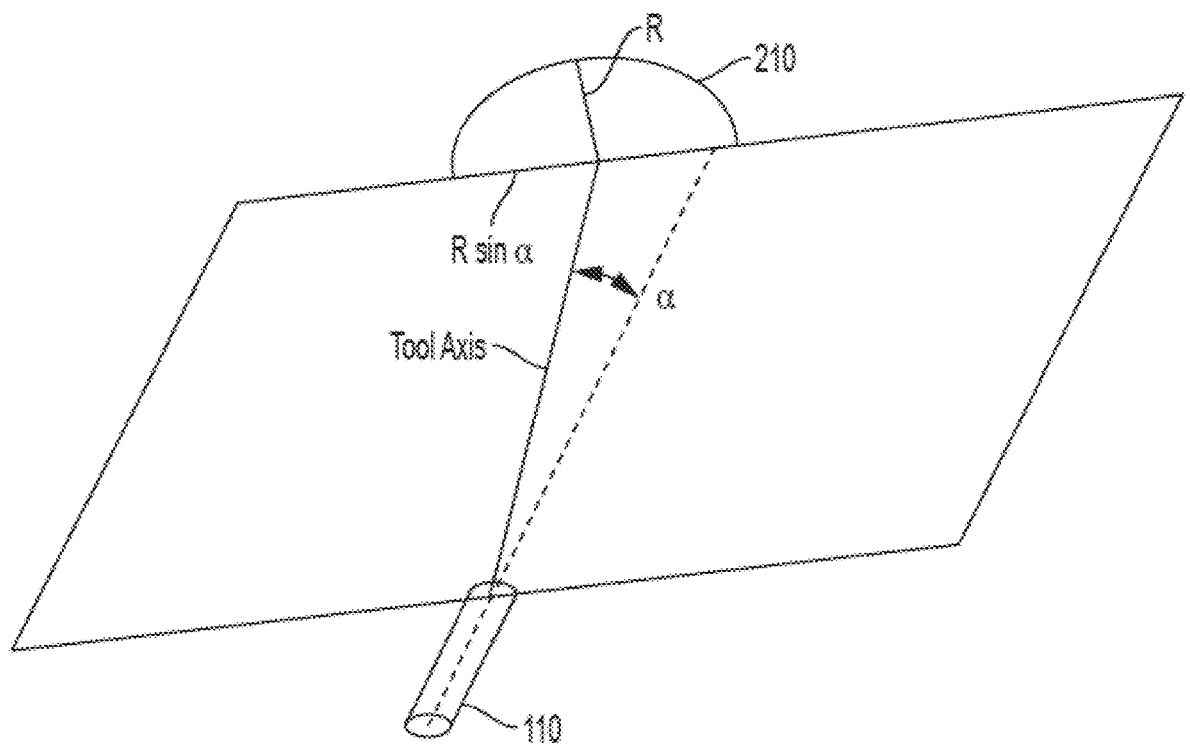
FIG. 11 is a schematic view of a tracking element configured for use with the tool of FIG. 10.

The ratio of the largest diameter of the ellipse to the smallest diameter of the ellipse can provide the angle α via a basic trigonometric formula (see FIG. 11). In practice, α will be small because the diameter of tool 200 is close to that of surgical port 110. For example, a port that is 5 inches in length with a diameter 2 mm larger than the inserted tool will result in a maximum angle α of approximately 1 degree. Based on the geometric constraints and formulas described above, it is possible to localize an end of tool 200 in a coordinate system coupled to surgical port 110.

Figure 12:
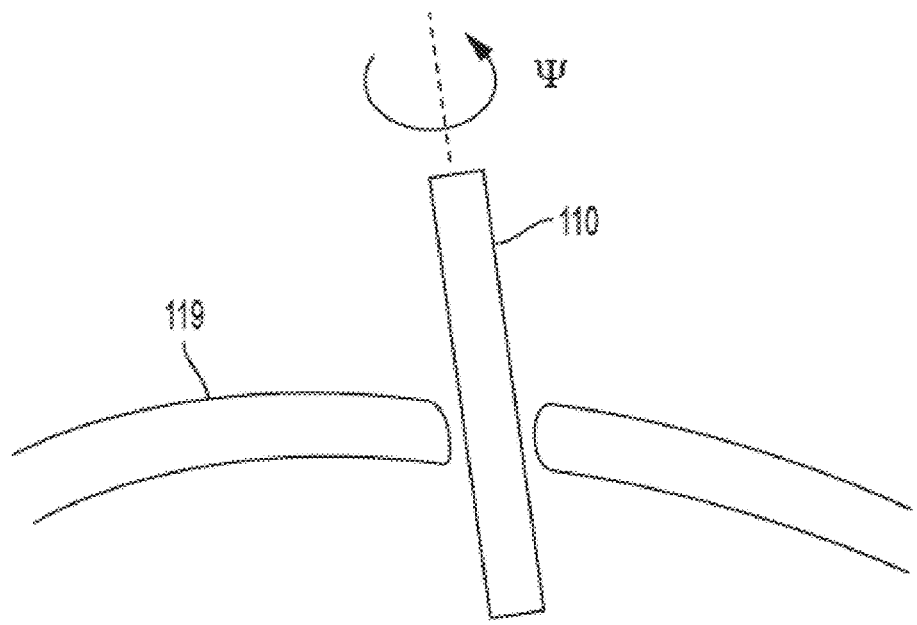
FIG. 12 is a schematic diagram of a surgical port of the system of FIG. 8.
Figure 13:
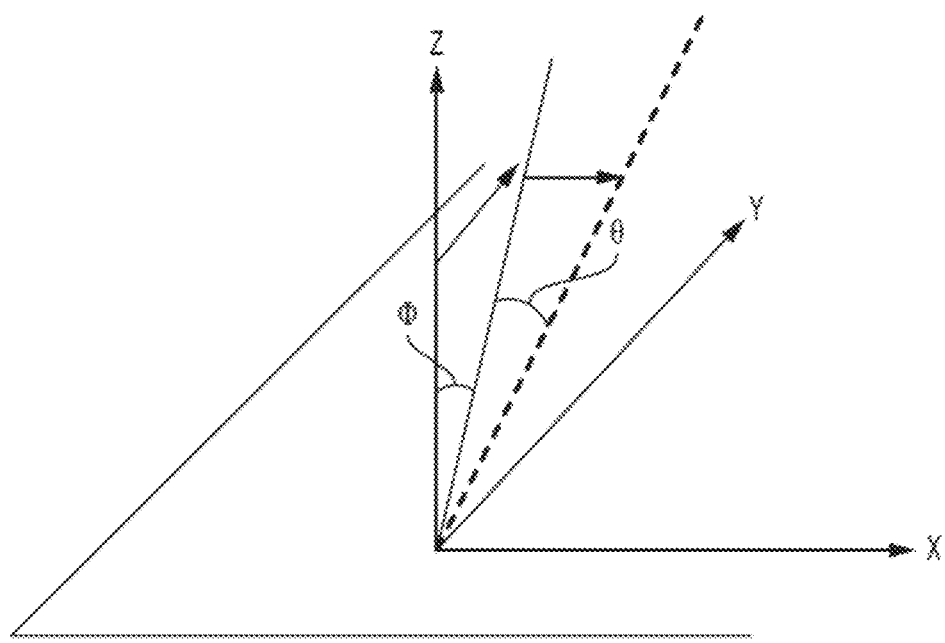
FIG. 13 is a schematic of the surgical port of the system of FIG. 8 in a coordinate system.

Surgical port 110 can have complex motion in three dimensions. Referring now to FIG. 12, the body of a patient 119 has elasticity, and port 110 can change angle in two independent spatial directions. The motility of patient 119 (e.g. an abdominal wall) can be used by the surgeon to direct the end of tool 200 in the region of interest (ROI). The orientation of the axis of port 110 in the (x, y, z) coordinate system of the operating room corresponds to two unknown angles denoted θ and Φ in FIG. 13. In addition, patient 119 or the support surface (e.g. operating room table) can move during the procedure due to breathing or other movements. Larger movements may correspond to the fact that the surgeon modified the angle of inclination of the support surface to facilitate access to the region of interest. The displacement of location at which port 110 enters patient 119 in three spatial directions is denoted by dx, dy, and dz.

Figure 14:
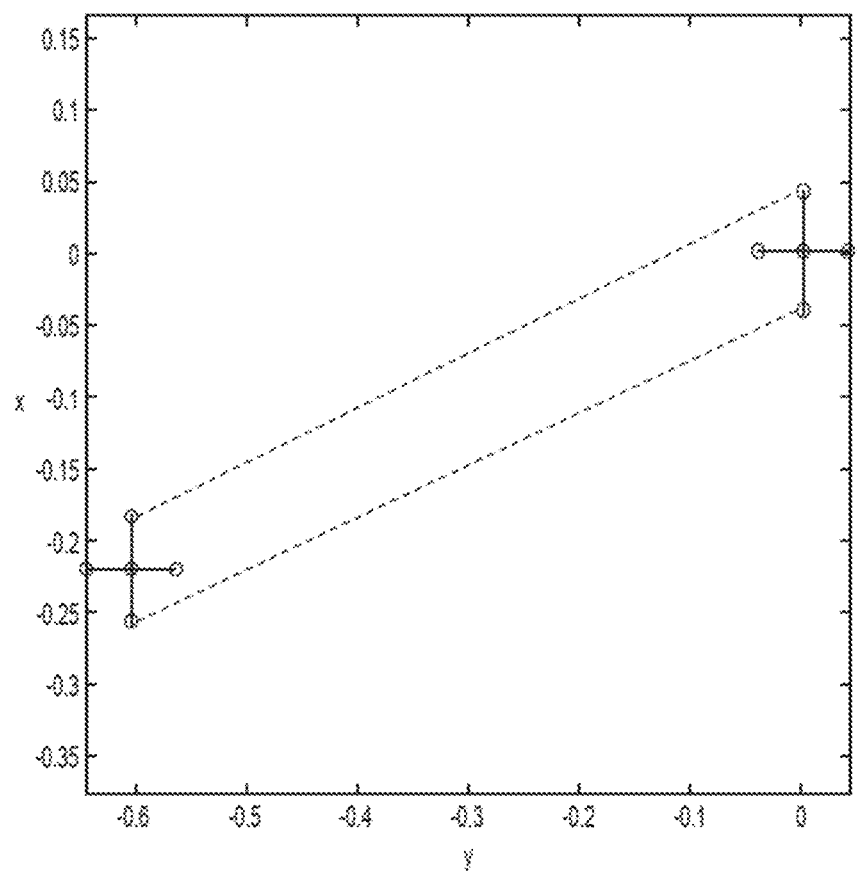
FIG. 14 is a graph of the trajectory of a reference marker of the system of FIG. 8.

Referring now to FIG. 14, image data (e.g. captured by camera 120) associated with a cross-shaped reference marker (e.g. one of reference markers 131-138) is displayed. From this image data, one can extract the trajectory of five points corresponding to the end points of the intersecting segments and the center of the reference marker. This trajectory corresponds to the motion of surgical port 110. As shown in the sections below entitled "A1 Method" and "A2 Experiment", mathematical calculations can be performed to determine θ, Φ, dx, dy, and dz. With these values known, one can then reconstruct the spatial trajectory of surgical port 110 in a coordinate system established, for example, in an operating room.

Combining the above parameters and calculations can provide a complete three-dimensional, real-time positioning system for a rigid laparoscopic tool and the tip or end of the tool.

In general, if the tool has mobile parts such as a scissor insert as shown in FIG. 10, one will need to identify the motion of the mobile parts versus the main body of the tool. In many cases, this can be done with a single degree of freedom. One can reconstruct the angle of the opening of the scissor from the image data (e.g. video streaming from an endoscope) to fully reconstruct the position of the tool. Simulated results indicate that accuracy can be obtained on the order of one millimeter for the position of a tool inside an abdominal cavity, and preliminary experimental results confirm the theoretical result.

In certain embodiments, the view angle of camera 120 may be limited and/or obstructed. It may therefore be desirable to include a plurality of reference markers on the ceiling of the operating room. Such a configuration can help to ensure that the system has sufficient input data and can ensure accuracy since the system can use redundant computation. In certain embodiments, the least square fitting method can be used to limit the impact of errors in the pattern recognition of the reference markers. This redundancy may also be used to correct optical distortion when the reference markers are far from the optical axis of the camera. Similarly, in the unlikely event that the surgical port rotates in the plan perpendicular to its axis, one can retrieve the angle of rotation (ψ) as shown in FIG. 12, since there will be multiple reference marker shapes (e.g. crosses of intersecting segments) to reconstruct the additional unknown.

It has been observed that an approximation of the position of a patient abdominal wall can be obtained by virtue of the smart trocars attached to the wall. Provided that one has a three-dimensional reconstruction of the anatomy of the patient in the operating room, one can position the tip of the laparoscopic tool with respect to anatomical structures. The operating room system should then be able to provide information to the surgeon on locations that should not be crossed by the crossed by the laparoscopic tool (e.g. a "secure no fly zone" used in training, but not currently in actual clinical conditions). Similarly, if an optimum access position has been decided during preparation of the operation, the system can guide the surgeon to that optimum maneuver.

Embodiments disclosed herein provide a low cost system that does not require new techniques from the surgeon. In addition, the system is robust and accurate, can be installed in a standard operating environment. The system also does not present additional risks to patients.

It is understood that the methods and mathematical models described in the sections below are exemplary of one embodiment, and that other embodiments are contemplated in this disclosure. For example, while a trocar is referenced in the discussion below, other types of surgical ports may be used in other embodiments.

A1 Method

For clarity, most of the mathematical presentation below is restricted first to motion in the vertical plane (x,z) that contain trocar. We will discuss briefly second the generalization to three spatial dimension in the (x,y,z) coordinate system of the OR.

Rotation:

Let us consider a rotation of the trocar clockwise in the (x,z) plane. We note this rotation $T_\theta$. The trocar has a fixed point that is the center of the rotation. Let is assume the trocar and the marker denoted by the triplet $(x_{-1}, x_0, x_1))$ are in the same vertical plane.

We consider first the direct problem: given θ, what would be the position of the marker in the new image?

Figure 15:
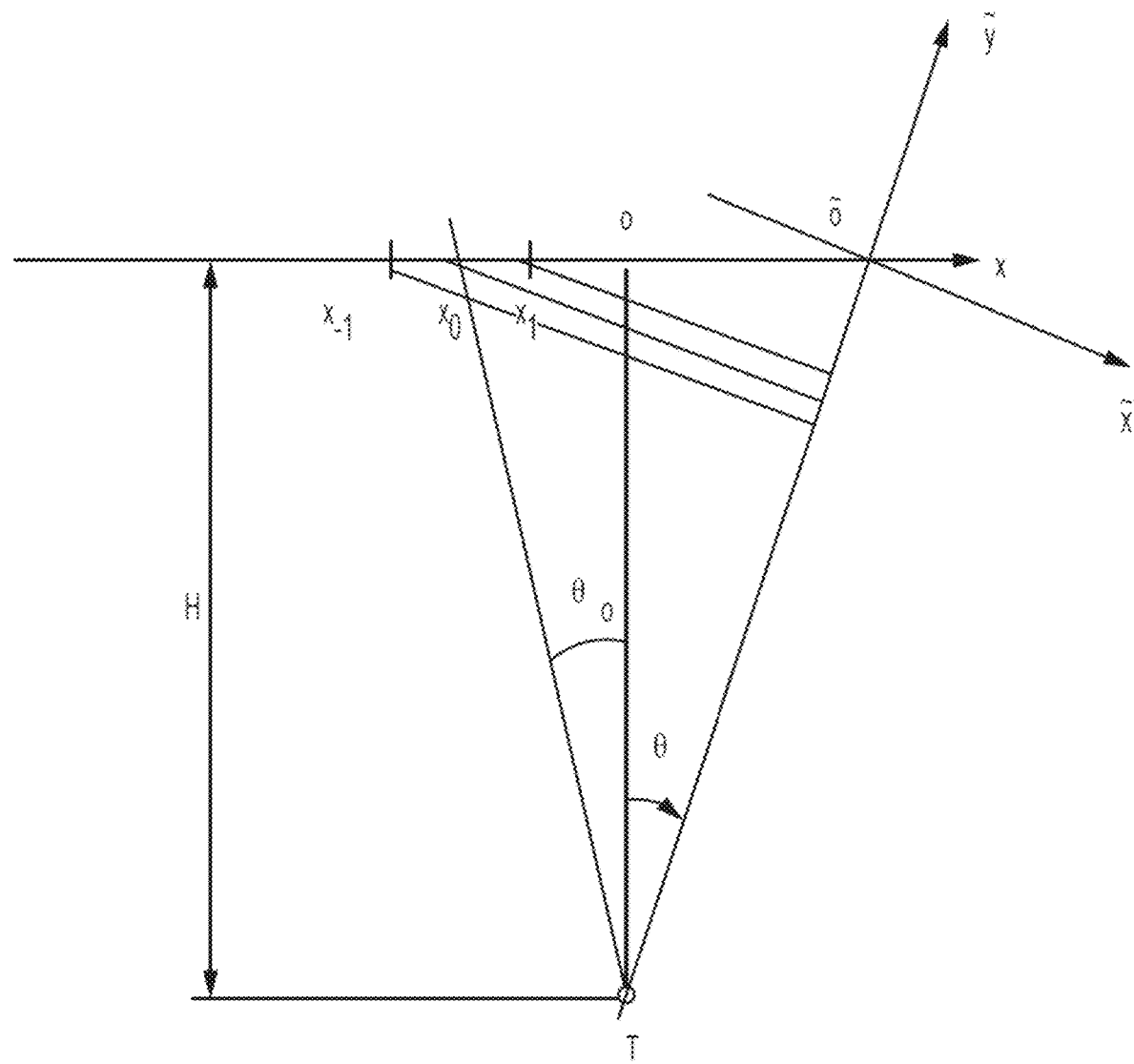
FIG. 15 is a schematic of the rotation of the surgical port of the system of FIG. 8.

In the new coordinate system $(\tilde{x}, \tilde{y})$—see FIG. 15—the coordinate of the marker $(x_{-1}, x_0, x_1))$, is, for j=−1, 0, 1:

$$\tilde{x}_j = \cos(\theta)(-H\tan(\theta)+x_j), \quad (1)$$

$$\tilde{y}_j = \sin(\theta)(-H\tan(\theta)+x_j), \quad (2)$$

Figure 16:
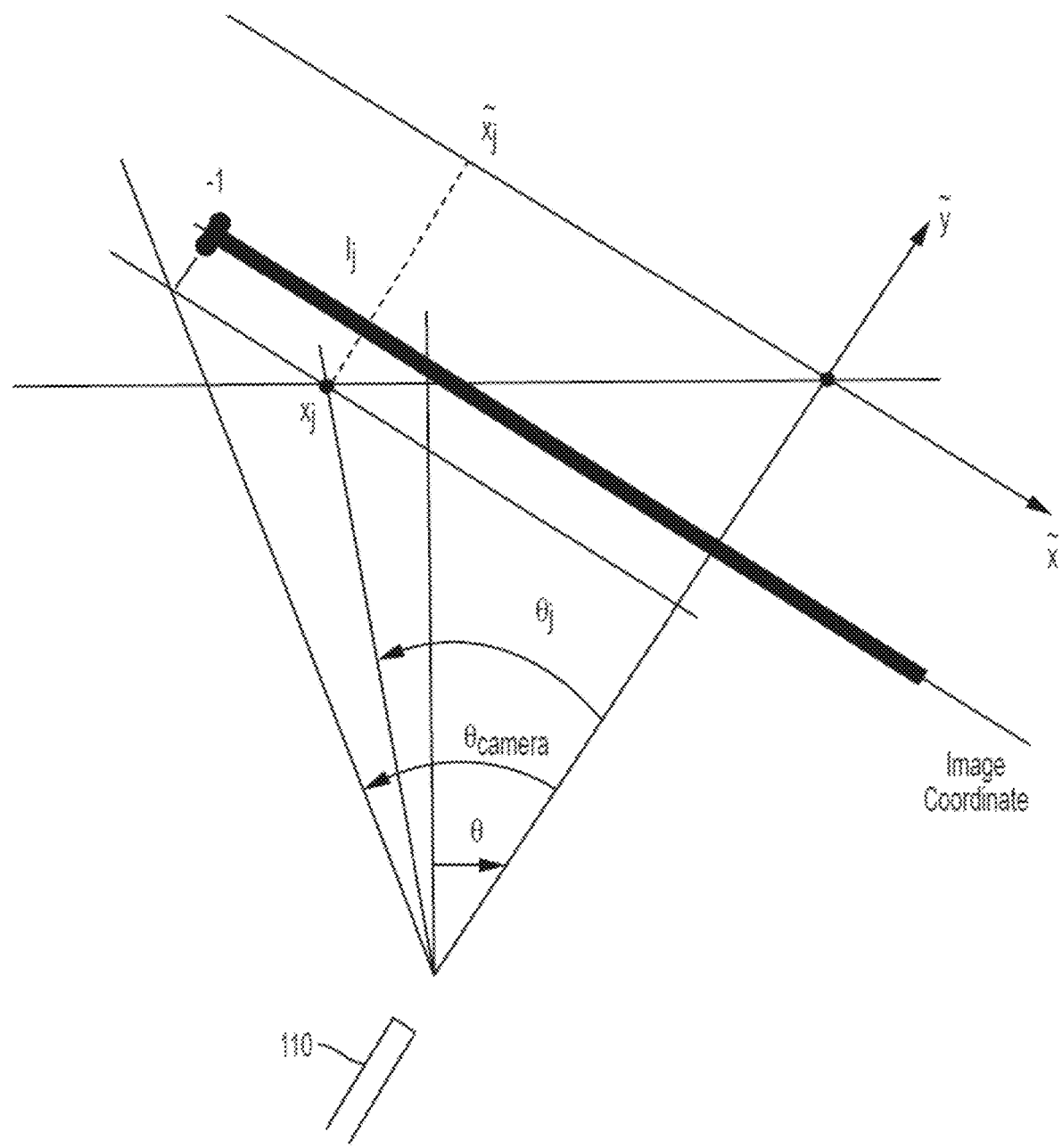
FIG. 16 is a schematic of the relationship of the surgical port of the system of FIG. 8 to new image coordinates.
Figure 17:
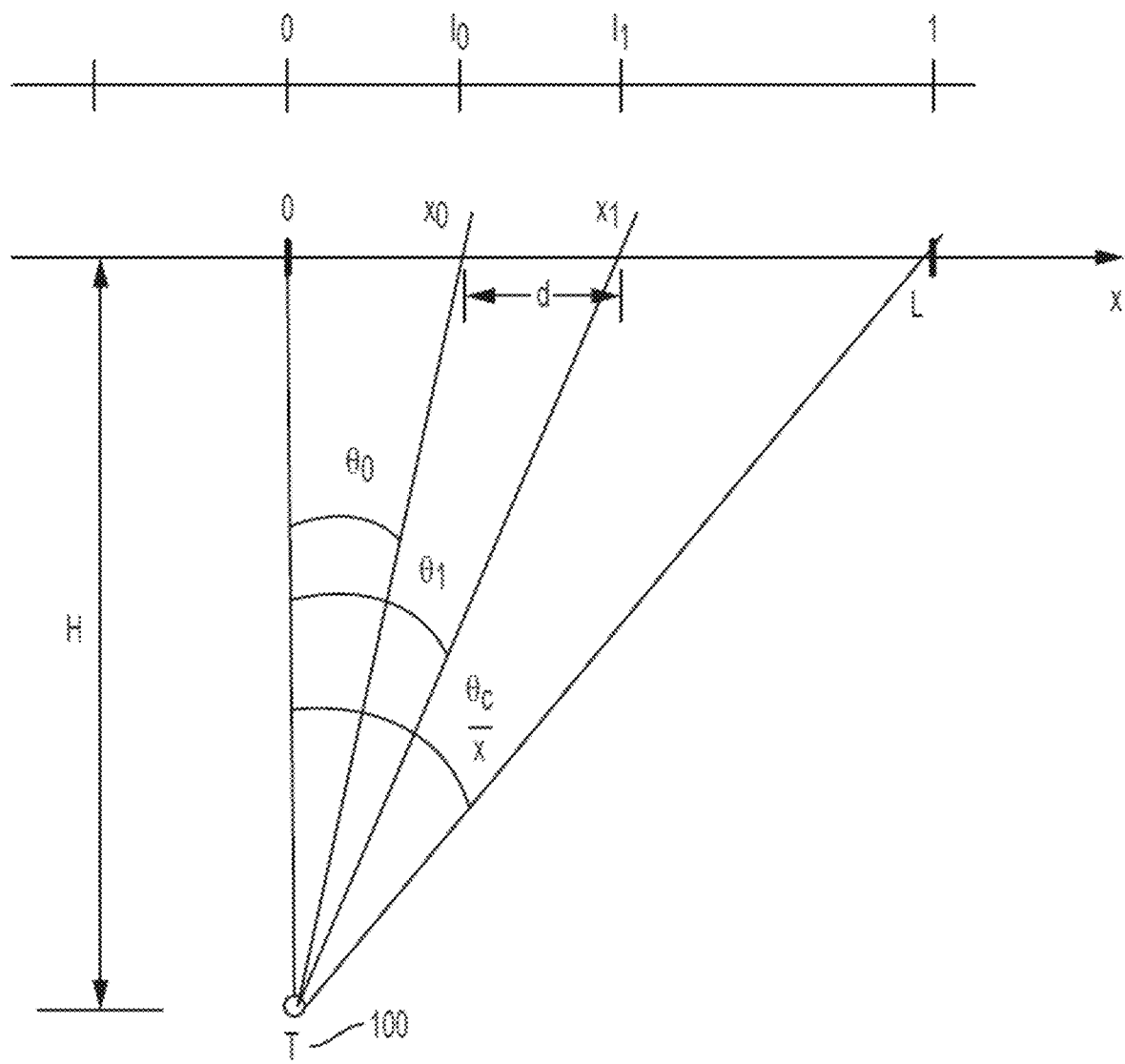
FIG. 17 is a schematic of the initial reconstruction of the coordinates of the surgical port of FIG. 8.

Let us denote $\Theta_c$ the view of the angle of the camera—see FIG. 16—The physical dimension of the new image frame is $(-\tilde{L}, \tilde{L})$, on the line $\tilde{y}=\tilde{y}_j$, is:

$$\tilde{L} = \tan\left(\frac{\Theta_c}{2}\right)\left(\frac{H}{\cos(\theta)} + \tilde{y}_j\right). \quad (3)$$

The position of the marker $x_j$ in the image (−1, 1) will be $$\tilde{I} = \frac{\tilde{x}_j}{\tilde{L}}. \quad (4)$$

For any landmark of coordinate $x_j$ in the initial image, the map $$\theta \to \tilde{I}_j(x_j)$$

for the range of rotation we do consider is bijective. As a matter of fact this map is a strictly decreasing function of θ. The inverse problem consist to solve the non linear set of equation (1) to (4) with for example a Newton scheme.

However we have assumed that the initial position of the trocar in the OR was given. Let us show that this problem can be solved with two landmarks—see FIG. 17. The two unknown are the physical location of the point O at the vertical of the trocar and the ceiling denoted H. For simplicity we will still restrict ourselves to the (x,z) plane. The generalization to 3D is straightforward.

To start we get the coordinate $I_o$ and $I_I$ of the landmark $x_0$ and $x_1$ in the image. We know also a priori the physical dimension $d=x_1-x_0$, of our marker.

We have:

$$\tan(\theta_0) = \frac{x_0}{H}, \tan(\theta_1) = \frac{x_1}{H}, \tan\left(\frac{\theta_c}{2}\right) = \frac{L}{H}. \quad (5)$$

and $$x_0 = I_0 L, x_1 = I_1 L. \quad (6)$$

We obtain:

$$H = d\left((I_1 - I_0)\tan\left(\frac{\theta_c}{2}\right)\right)^{-1}.$$

and $$x_0 = I_0 H \tan\left(\frac{\theta_c}{2}\right), x_1 = I_1 H \tan\left(\frac{\theta_c}{2}\right).$$

This concludes the reconstruction of the rotation of the trocar by tracking the landmarks on the ceiling.

However the motion of the trocar can be more complex and involve two translations in respectively x and z direction. We will denote dx and dz this displacement and as before θ the rotation.

Translation:

To take into account these two translations, denoted $T_{dx}$ and $T_{dz}$, the landmark of the initial coordinate $x_j$ has for new coordinates $$\tilde{x}_j = \cos(\theta)(-H-dz\tan(\theta)+x_0-dx), \quad (7)$$

$$\tilde{y}_j = \sin(\theta)(-H-dz\tan(\theta)+x_0-dx), \quad (8)$$

We have now three unknowns that are dx and dy and θ. We need then three landmarks. We need to solve the nonlinear set of equations with the image coordinate $I_{-1}, I_0, I_1$ from these landmarks. We can now use Newton scheme to solve numerically that non linear problem, since we can explicitly compute the Jacobian of the system. So far we have restricted ourselves to two space dimension and we worked with a combination of the three geometric transform:

$$T_\theta \circ T_{dx} \circ T_{dz}.$$

A similar reasoning can be applied in three space dimensions. We consider the three d coordinate systems (x,y,z) of the OR. We work with the transformation:

$$T_\theta \circ T_\phi \circ T_{dx} \circ T_{dy} \circ T_{dz}.$$

We need then to identify 5 unknowns θ, φ, dx, dy, dz and will need 5 landmarks. We wrote with a MATLAB® code a small simulator based in a cross motif—see FIG. 15. This code applies successively each transformation to the image viewed from the trocar. This simulator helps us compute the sensitivity of the system. Let us assume that the image comes with a resolution of 500 pixels in each dimension. One can show from simulation that an accumulated error of 4 pixel in each spatial direction will result in an error of about 1 mm at the end of the laparoscopic tool. This error is very small indeed because the relative distance from the trocar to the ceiling is much larger than from the trocar to the ROI inside the abdominal cavity.

The exact accuracy of the system needs to be checked with an experiment that will carry various types of uncertainties, from optical defect of the camera, imperfection in focussing, and noise in the image segmentation of the landmark. We expect however to have a fairly robust and accurate result from our design. Next we will present some preliminary experimental results that validate our approach.

A2 Experiment

Our goal here is to validate the quality of the method to reconstruct separately each component of the motion of the trocar, from tracking the landmark on the ceiling.

Figure 18:
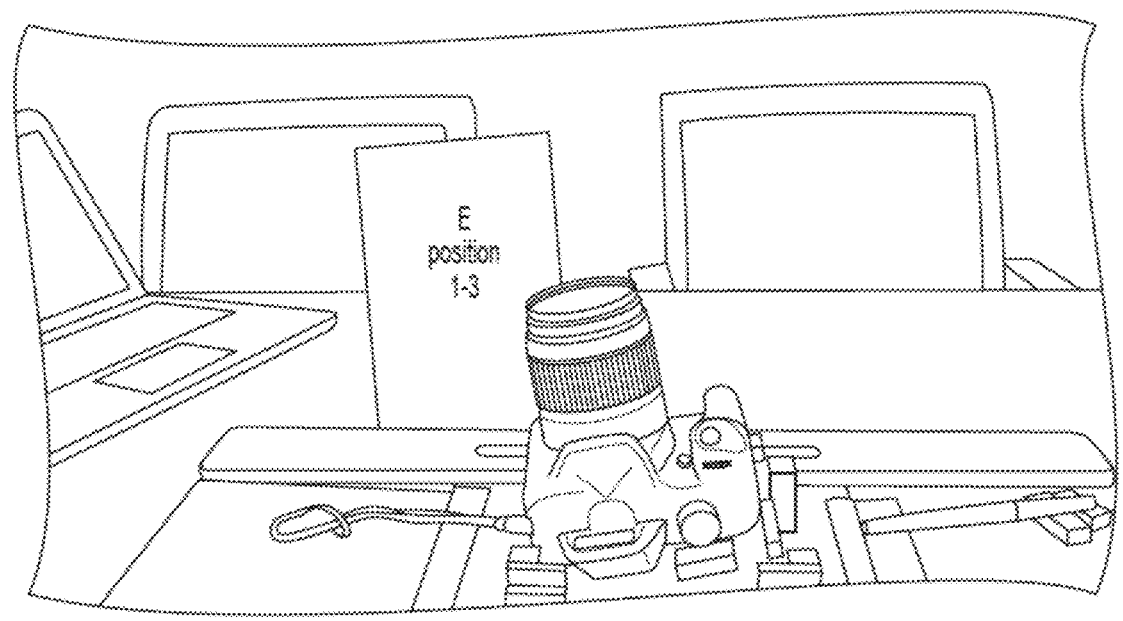
FIG. 18 is a photograph of the camera used to validate data acquired by the system of FIG. 8.
Figure 19:
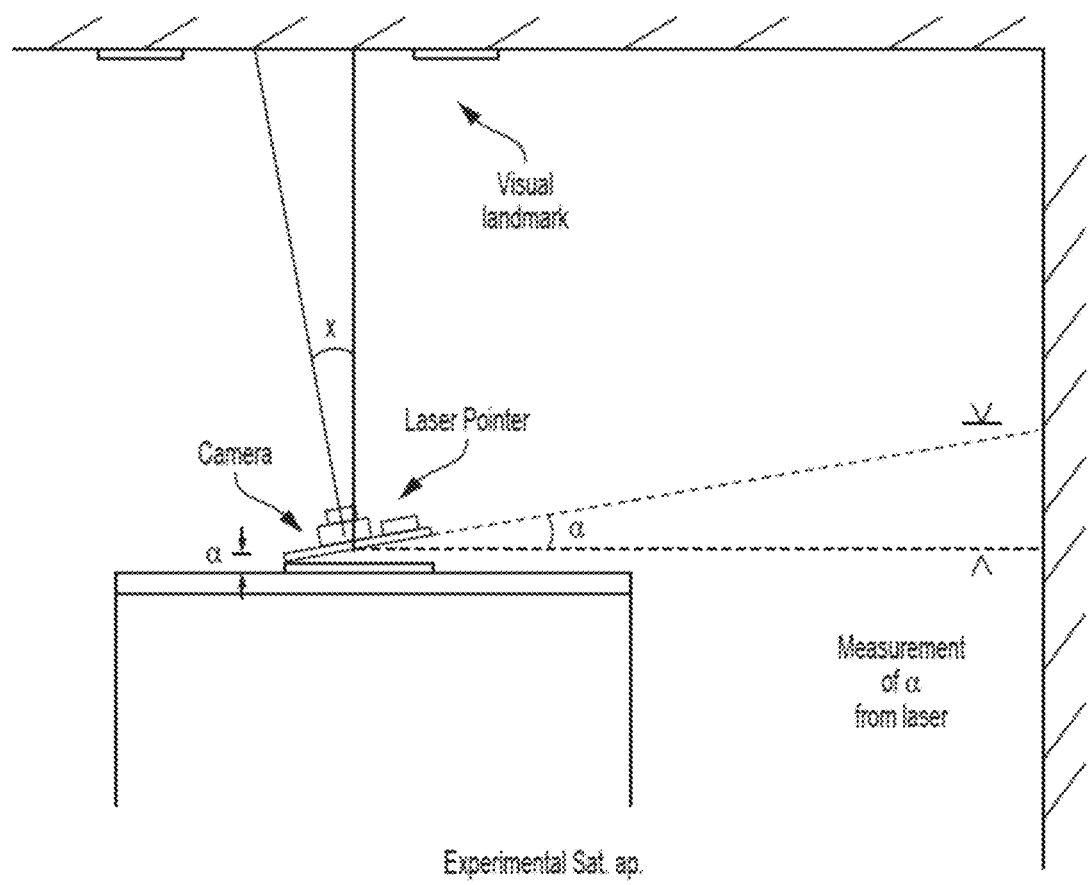
FIG. 19 is a schematic of the camera of FIG. 18.

Rotation:

Let's start with the rotation component in one space dimension. FIG. 18 and FIG. 19 show a rapid prototyping to check that result.

Figure 20:
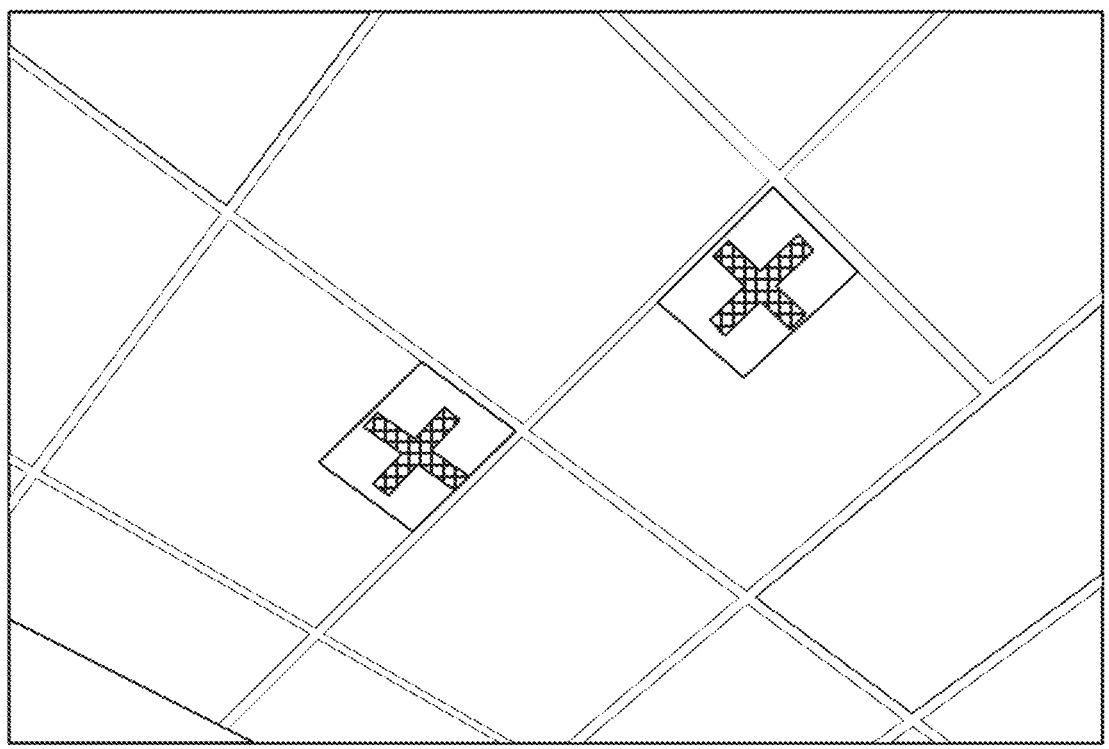
FIG. 20 is a photograph of reference marks.
Figure 21:
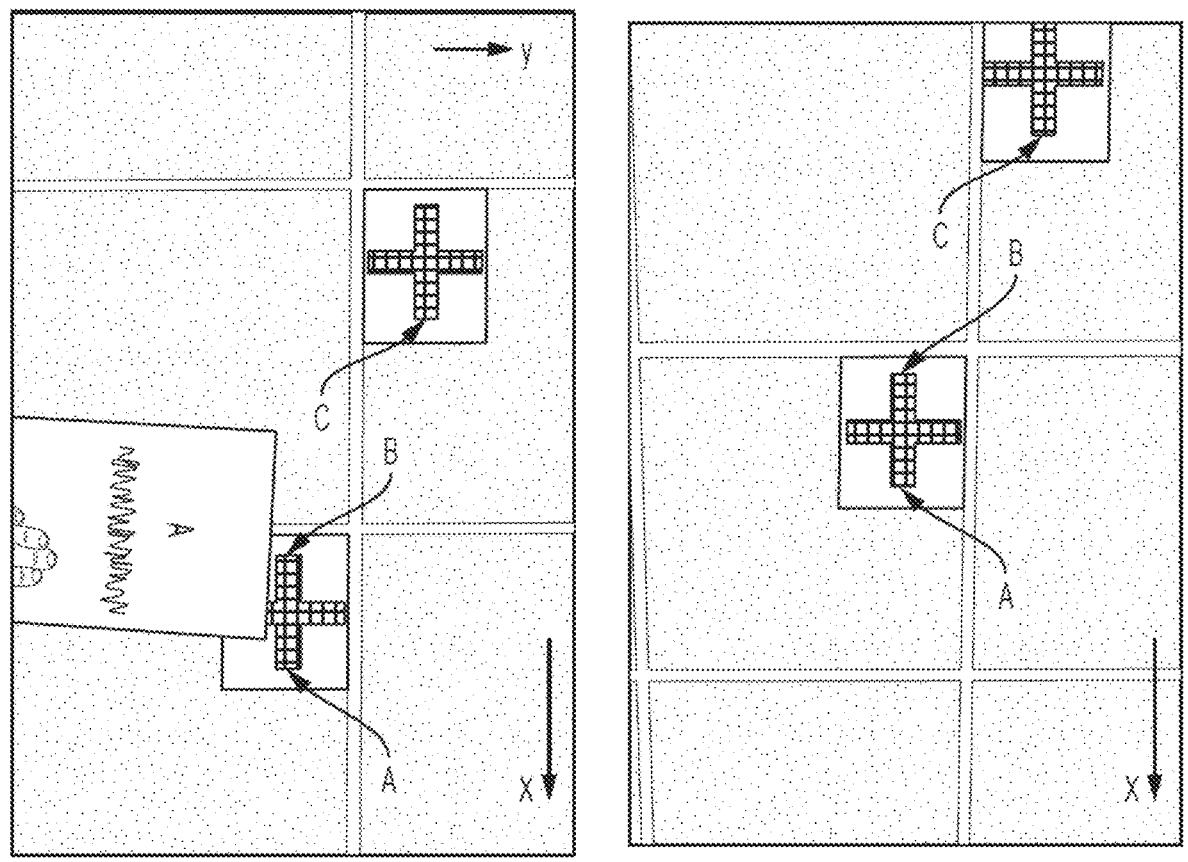
FIG. 21 is a photograph of reference marks before and after rotation.

We have set on the ceiling two black crosses that are visible from the digital camera—see FIG. 20. We set first the camera in a flat position, and measure on the wall height of the laser beam projection. We shoot in that position an image of the ceiling.—see FIG. 21 on left. The auto focus option of the camera was turned off. The image of the ceiling is somehow out of focus. We made this image noisy on purpose to get more realistic conditions.

We set the second camera in a position that forms a small angle with the desk as in FIG. 18. We measure on the wall the new position of the laser beam projection. From these two measures on the wall, we get the angle α with an accuracy of about 0.5°. We shoot in that new position an image of the ceiling—see FIG. 21 on right.

We observe indeed the displacement of the markers due to the change of orientation of the camera.

We apply then our algorithm to reconstruct the angle α from these two images: first we compute the coordinate of the three points A, B, and C using the graphic interference of the GIMP2 software. An automatic image segmentation will be actually more accurate.

Figure 22:
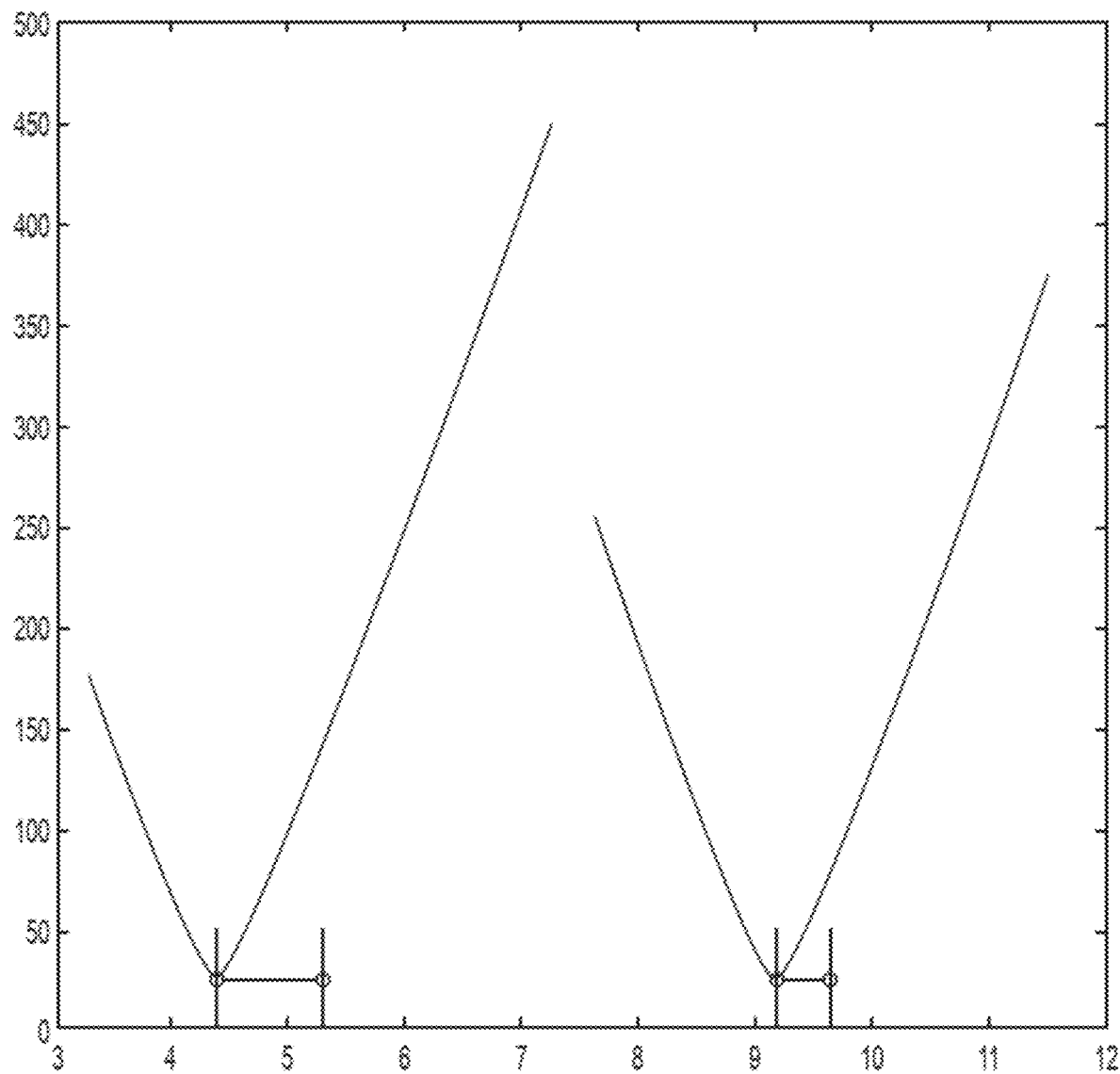
FIG. 22 is a graph of a computational result with different angles.

Second we map the transformation we defined earlier $$\theta \rightarrow \tilde{I}_j(x_j)$$

and look for the angle that minimizes the matching between the compound coordinate of the point A, B and C after rotation, in the L2 norm—FIG. 22. Our results are for α=5.3° and α=9.6°. Our algorithm based on computer vision gives: α=4.4° and α=9.2°. We did this experiment several times, and observed a good reliability of the method.

In other words we get an error of less than a degree on the trocar position. This may represent an error on the lateral position of the tip of a laparoscopic tool of the order of 3 mm for a ROI with a 20 cm depth from the abdominal wall.

Translation:

Next let us consider a different displacement of the trocar that can be for example resulting from a patient breathing.

We have run a similar experiment to check the accuracy of a displacement of the "trocar" in the vertical direction z toward the ceiling. Here the camera stays flat, and we change the thickness of the support, to increase the height of a few centimeters. Let's denote δz the increase in thickness of the support. For δz=2 cm we get from our computer vision algorithm a value of δz=1.62 cm. Similarly for δz=3 cm we get from our computer vision algorithm a computed value of δz=3.23 cm. Overall the error on the vertical displacement is less than 4 mm. We suspect that we can improve much that result by using landmarks separated by larger distances.

While the foregoing description and drawings represent examples of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed examples are, therefore, to be considered in all respects as illustrative and not restrictive, the scope of the invention being indicated by the appended claims and not limited to the foregoing description.

It will be appreciated by those skilled in the art that changes could be made to the examples described above without departing from the broad inventive concept thereof. It is understood, therefore, that this invention is not limited to the particular examples disclosed, but it is intended to cover modifications within the spirit and scope of the present invention, as defined by the following claims.

REFERENCES

The contents of the following references are incorporated by reference herein:

U.S. Provisional Patent Application 61/734,506.
WO 2014/089439.
3D IRCAD Liver Data Base http://www.ircad.fr/softwares/3Dircadb/3Dircadb1/?lng=en
Agarwal S, Joshi A, Finin T, Yesha Y 2007). A Pervasive Computing System for the Operating Room of the Future. *Mobile Networks and Applications;* 12:215-28.
Aggarwal R, Moorthy K, and Darzi A (2004). Laparoscopic skills training and assessment. *Br J Surg;* Vol. 91, No. 12, pp. 1549-58.
Allan M, Ourselin S, Thompson S, Hawkes D J, Kelly J and Stoyanov D (2013). Toward detection and localization of instruments in minimally invasive surgery. *Biomedical Engineering. IEEE Transactions;* Vol. 60, No. 4, pp. 1050-1058.
Asano, T K, Soto, C, Poulin E C, Mamazza, J, and Boushey R P (2011). Assessing the impact of a 2-day laparoscopic intestinal workshop. *Can J Surg,* 4, pp. 223-6.
Bano J, Hostettler A, Nicolau S, Cotin S, Doignon C, Wu H S, Huang M H, Soler L, Marescaux J (2012). Simulation of Pneumoperitoneum for Laparoscopic Surgery Planning. *MICCAI;* Vol. 7510, pp. 91-98.
Bardram J E, Doryab A, Jensen R M, Lange P M, Nielsen K L G, and Petersen S T (2011). Phase recognition during surgical procedures using embedded and body-worn sensors. *PerCom;* pp. 45-53.
Blasinski H, Nishikawa A, and Miyazaki F (2007). The application of adaptive filters for motion prediction in visually tracked laparoscopic surgery. *Robotics and Biomimetics, ROBIO 2007; IEEE International Conference;* pp. 360-365.
Blum T, Padoy N, Feussner H, and Navab N (2008). Modeling and online recognition of surgical phases using Hidden Markov Models. *Med Image Comput Comput Assist Interv;* 11:627-35.
Blum T, Padoy N, Feussner H, Navab N. (2008). Modeling and online recognition of surgical phases using Hidden Markov Models. *Med Image Comput Comput Assist Interv;* 11:627-35.
Breedveld P, Stassen H, Meijer D W, and Jakimowicz J J (2000). Observation in laparoscopic surgery: overview of impeding effects and supporting aids. *J Laparoendosc Adv Surg Tech;* Vol. 10, No. 5, pp. 231-41.
Bucholz R D, Yeh D D, Trobaugh J, McDurmott L L, Sturm C D, Baumann C, Henderson J M, Levy A, and Kessman P. (1997). The correction of stereotactic inaccuracy caused by brain shift using an intraoperative ultrasound device. *Lecture Notes in Computer Science (MICCAI);* Vol. 1205, No. 1997, pp. 459-66.
Carter T J, Sermesant M, Cash D M, Barratt D C, Tanner C, and Hawkes D J (2005). Application of soft tissue modelling to image-guided surgery. *Med Eng Phys;* Vol. 27, No. 10, pp. 893-909.
Climent J and Mares P. (2003). Real-time tracking system for assisted surgical operations. *Latin America Transactions, IEEE (Revista IEEE America Latina);* 1(1): 8-14.

Colombo, J R, Haber, G P Jr, Rubinstein M, and Gill I S (2006). Laparoscopic surgery in urological oncology: brief overview. *Int Braz J Urol;* 32(5):504-12.

Doryab A, and Bardram J E (2011). Designing activity-aware recommender systems for operating rooms. *Proceedings of the Workshop on Context-awareness in Retrieval and Recommendation,* pp; 43-6.

Doryab A, Togelius J, and Bardram J (2012). Activity-aware recommendation for collaborative work in operating rooms. *Proceedings of the ACM international conference on Intelligent User Interfaces;* pp. 301-4.

Dutkiewicz P, Kielczewski M, and Kowalski M. (2004). Visual tracking of surgical tools for laparoscopic surgery. *Robot Motion and Control, 2004. RoMoCo '04. Proceedings of the Fourth International Workshop;* pp. 23-28.

Dutkiewicz P, Kietczewski M, Kowalski M, and Wroblewski W (2005). Experimental verification of visual tracking of surgical tools. *Robot Motion and Control, RoMoCo '05. Proceedings of the Fifth International Workshop;* pp. 237-242.

Estebanez B, del Saz-Orozco Rivas P I, Bauzano E, Muoz V F and Garcia-Morales I, (2012). Maneuvers recognition in laparoscopic surgery: Artificial Neural Network and hidden Markov model approaches. *4th IEEE RAS & EMBS International Conference on Biomedical Robotics and Biomechatronics;* pp. 1164-1169.

Fasquel J, Brocker G, Moreau J, Agnus V, Papier N, Koehl C, Soler L, and Marescaux J (2006). A Modular and Evolutive Software for Patient Modeling Using Components, Design Patterns and a Formal XML-Based Component Management System. *CBMSm 19th IEEE International Symposium;* pp. 43-50.

Franco D, (2001), Right hepatectomy, WeBSurg.com; 1(12).

Garbey, M, Salmon R, Thanoon D, Bass B (2013). Multi-scale Modeling and Distributed Computing to Predict Cosmesis Outcome After a Lumpectomy. *J. Comput. Physics;* 244: 321-335.

Gould J, and Frydman J (2007). Reverse-alignment surgical skills assessment. *Surgical Endoscopy;* Vol. 21, No. 4, pp. 669-671.

Hawkes D J, Barratt D, Blackall J M, Chan C, Edwards P J, Rhode K, Penney G P, McClelland J and Hill D L G. (2005). Tissue deformation and shape models in image-guided interventions: a discussion paper. *Medical Image Analysis;* Vol. 9, No. 2, pp. 163-75.

Herron D, Gagner M, Kenyon T, and Swanström, L (2001). The minimally invasive surgical suite enters the 21st century. *Surgical Endoscopy;* Vol. 15, No. 4, pp. 415-422.

Hodgson A J, Pantazopol, R A, Visser, M D, Salcudean, S E, and Nagy, A G, (1997). "Assessing potential benefits of enhanced dexterity in laparoscopic surgery." *Engineering in Medicine and Biology Society. Proceedings of the 19th Annual International Conference of the IEEE;* Vol. 5, pp. 1966-1969.

Ikuta K, Kato T, Ooe H, and Ando S. (2007). Surgery recorder system for recording position and force of forceps during laparoscopic surgery. *Advanced intelligent mechatronics, 2007 IEEE/ASME international conference;* pp. 1-6.

Jakimowicz J J, and Ruers T J M (1991). Ultrasound-Assisted Laparoscopic Cholecystectomy: Preliminary Experience. *Dig Surg;* Vol. 8(2), pp. 114-17.

Jakimowicz J J. (2006). Intraoperative ultrasonography in open and laparoscopic abdominal surgery: an overview. *Surg Endosc,* Vol. 20 Suppl 2, pp. S425-35.

Konishi K, Nakamoto M, Kakeji Y, Tanoue K, Kawanaka H, Yamaguchi S, Ieiri S, Sato Y, Maehara Y, Tamura S, and Hashizume M. (2007). A real-time navigation system for laparoscopic surgery based on three-dimensional ultrasound using magneto-optic hybrid tracking configuration. *IJCARS;* Vol. 2, No. 1, pp. 1-10.

Kranzfelder M, Schneider A, Blahusch G, Schaaf H, and Feussner H (2009). Feasibility of opto-electronic surgical instrument identification. *Minim Invasive Ther Allied Technol;* 18(5):253-8.

Kranzfelder M, Schneider A, Gillen S, and Feussner H (2011). New technologies for information retrieval to achieve situational awareness and higher patient safety in the surgical operating room: the MRI institutional approach and review of the literature. *Surg Endosc;* Vol. 25, No. 3, pp. 696-705

Kühnapfel U, çakmak H K, and Maass H. (2000). Endoscopic surgery training using virtual reality and deformable tissue simulation. *Computer & Graphics,* Vol. 24, No., pp. 671-82.

Langø T, Tangen G A, Mårvik R (2012). Navigated ultrasound in laparoscopic surgery. *Advances in Laparoscopic Surgery;* pp. 77-98.

Liu C C, Chang C H, Su M C, Chu H T, Hung S H, JWong J M, and Wang P C (2010). RFID-initiated workflow control to facilitate patient safety and utilization efficiency in operation theater. *Comput Methods Programs Biomed;* 3, pp. 435-42.

Liu C C, Chang C H, Su, M C, Chu H T, Hung S H, Wong J M and Wang P-C (2011). RFID-initiated workflow control to facilitate patient safety and utilization efficiency in operation theater. *Comput Methods Programs Biomed;* 104(3):435-42.

Mackay S, Datta V, Chang A, Shah J, Kneebone R, and Darzi A (2003). Multiple Objective Measures of Skill (MOMS): a new approach to the assessment of technical ability in surgical trainees. *Ann Surg;* 2, pp. 291-300.

Mahmoud N, Nicolau S, Keshk A, Ahmad M A, Soler L, Marescaux J (2012). Fast 3D Structure From Motion with Missing Points from Registration of Partial Reconstructions. *AMDO;* pp. 73-183.

Marjamaa R, Vakkuri A, and Kirvel Ä O (2008). Operating room management: why, how and by whom? *Acta Anaesthesiologica Scandinavica;* 52:596-600.

Mårvik R, Langø T, Tangen G A, Andersen J O, Kaspersen J H, Ystgaard B, Sjølie E, Fougner R, Fjøsne H E, and Hernes T A. (2004). Laparoscopic navigation pointer for 3-D image guided surgery. *Surg Endosc;* Vol. 18, No. 8, pp. 1242-8.

Nakamoto M, Hirayama H, Sato Y, Konishi K, Kakeji Y, Hashizume M, and Tamura S. (2007). Recovery of respiratory motion and deformation of the liver using laparoscopic freehand 3D ultrasound system. Medical Image Analysis; Vol. 11, No. 5, pp. 429-42.

Nakamoto M, Nakada K, Sato Y, Konishi K, Hashizume M, and Tamura S (2008). Intraoperative Magnetic Tracker Calibration Using a Magneto-Optic Hybrid Tracker for 3-D Ultrasound-Based Navigation in Laparoscopic Surgery. *Medical Imaging, IEEE Transactions;* 27(2):255-270.

Navarro A A, Hernansanz A, Villarraga E A, Giralt X, and Aranda J (2007). Enhancing Perception in Minimally Invasive Robotic Surgery through Self-Calibration of Surgical Instruments. *Engineering in Medicine and Biology Society, EMBS 2007, 29th Annual International Conference of the IEEE;* pp. 457-460.

Neumuth D, Loebe F, Herre H, and Neumuth T (2011). Modeling surgical processes: a four-level translational approach. *Artif Intell Med. Netherlands;* 51(3):147-61.

Neumuth T, Jannin P, Schlomberg J, Meixensberger J, Wiedemann P, and Burgert O (2011). Analysis of surgical intervention populations using generic surgical process models. *Int J Comput Assist Radiol Surg;* 6:59-71.

Neumuth T, Jannin P, Strauss G, Meixensberger J, and Burgert O (2009). Validation of knowledge acquisition for surgical process models. *J Am Med Inform Assoc;* 16(1): 72-80.

Neumuth T, Strauss G, Meixensberger J, Lemke H, and Burgert O (2006). Acquisition of Process Descriptions from Surgical Interventions. *Database and Expert Systems Applications;* pp. 602-11.

Nicolau S, Mendoza-Burgos L, Soler L, Mutter D, Marescaux J (2008). In Vivo Evaluation of a Guidance System for Computer Assisted Robotized Needle Insertion Devoted to Small Animals. *MIAR;* pp 241-250.

Padoy N, Blum T, Ahmadi S-A, Feussner H, Berger M-O, and Navab N (2012). Statistical modeling and recognition of surgical workflow. *Medical Image Analysis;* 16:632-41.

Payandeh S, Xiaoli Z, and Li A. (2001). Application of imaging to the laproscopic surgery. *Computational Intelligence in Robotics and Automation, Proceedings 2001, IEEE International Symposium;* pp. 432-437.

Reddy S K, Tsung A, Geller D A. (2010) Laparoscopic Liver Resection. *World Journal of Surgery;* 35:1478-1486.

Reinertsen I, Lindseth F, Unsgaard G, and Collins D L (2007). Clinical validation of vessel based registration for correction of brain-shift. *Medical Image Analysis;* 11(6): 673-84.

Richardson W, Stefanidis D, Mittal S, and Fanelli R D (2010). SAGES guidelines for the use of laparoscopic ultrasound. *Surg Endosc;* 24:745-56.

Sarker S K, Chang A., and Vincent C (2006). Technical and technological skills assessment in laparoscopic surgery. *JSLS;* Vol. 10, No. 3, pp 284-92.

Scheuering M, Schenk A, Schneider A, Preim B, and Greiner G. (2003). Intraoperative Augmented Reality for Minimally Invasive Liver Interventions. *Proc SPIE;* Vol. 5029, pp. 407-17.

Schoepp H. Surgical Navigation System (2012).

Shahidi R, Bax M R, Maurer C R Johnson J A, Wilkinson E P, Wang B, West, J B, Citardi M J, Manwaring K H and Khadem R (2002). Implementation, Calibration and Accuracy Testing of an Image Enhanced Endoscopy System. *IEEE Trans Med Imaging;* Vol. 21, No. 12, pp. 1524-35.

*Society of American Gastrointestinal and Endoscopic Surgeons,* http://www.sages.org/

Soler L, Nicolau S, Fasquel J, Agnu V, d Charnoz A, Hostettler A, Moreau J, Forest C, Mutter D, and Marescaux J (2008). Virtual reality and augmented reality applied to laparoscopic and notes procedures. *ISBI;* pp. 1399-1402.

Staub C, Lenz C, Panin G, Knoll A, and Bauernschmitt R (2010). Contour-based surgical instrument tracking supported by kinematic prediction. *Biomedical Robotics and Biomechatronics (BioRob), 2010 3rd IEEE RAS and EMBS International Conference;* pp. 746-752.

Stoll J, Ren H and Dupont P E (2012). Passive Markers for Tracking Surgical Instruments in Real-Time 3-D Ultrasound Imaging. *IEEE Transactions on Medical Imaging;* Vol. 31, No. 3, pp. 563-575.

Tatar F, Mollinger J, Bossche A (2003). Ultrasound system for measuring position and orientation of laparoscopic surgery tools. *Sensors, Proceedings of IEEE;* Vol. 2, pp. 987-990.

Tatar F, Mollinger J R, Bastemeijer J, and Bossche A (2004). Time of flight technique used for measuring position and orientation of laparoscopic surgery tools. *Sensors,* 2004. *Proceedings of IEEE,* p. 1596.

Thanoon D, Garbey M. and Bass B L (2013). Deriving Indicators for Breast Conserving (BCS) using Finite Element Analysis (FEM). *Computer Methods in Biomechanics and Biomedical Engineering;* pp. 1-12.

Tsai C-C and Wang T-Y (2008). Small humanoid robot localization by landmarks. *7th World Congress on Intelligent Control and Automation;* pp. 6584-6589.

Uchida T, Koyama H, Komeda T, Miyagi M and Funakubo H (1996). Measuring method of three dimensional position and orientation of a moving object for medical robots, *IEEE International Conference on Systems, Man, and Cybernetics;* Vol. 2, pp. 887-892.

Unsgaard G, Rygh O M, Selbekk T, Müller T B, Kolstad F, Lindseth F, and Hernes T A. (2006). *Intra-operative 3D ultrasound in neurosurgery. Acta Neurochirurgica;* Vol. 148, No. 3, pp. 235-53.

Voros S, Orvain E, Cinquin P, and Long J A (2006). Automatic detection of instruments in laparoscopic images: a first step towards high level command of robotized endoscopic holders. *Biomedical Robotics and Biomechatronics, BioRob 2006. The First IEEE/RAS-EMBS International Conference;* pp. 1107-12.

Wein W, Khamene A, Clevert D-A, Kutter O, Navab N (2007). Simulation and Fully Automatic Multimodal Registration of Medical Ultrasound. *Medical Image Computing and Computer-Assisted Intervention—MICCAI 2007, Lecture Notes in Computer Science;* Vol. 4791, pp. 136-14.

Wolpert S, Bosseau Murray W, Gorman P J, and Bholat O S (1999). Movement trajectories in laparoscopic tools. *Engineering in Medicine and Biology. 21st Annual Conf and the Annual Fall Meeting of the Biomedical Engineering Soc. BMES/EMBS Conference. Proceedings of the First Joint;* Vol. 2.

Wytyczak-Partyka A, Nikodem J, Klempous R, Rozenblit J, Radoslaw Klempous, and Rudas I (2009). Safety Oriented Laparoscopic Surgery Training System. *Computer Aided Systems Theory—EUROCAST;* Vol. 5717, pp. 889-896.

Yuan J S-C (1989). A general photogrammetric method for determining object position and orientation. *IEEE Transactions on Robotics and Automation;* Vol. 5, Issue 2, pp. 129-142.

Zhu W, Nicolau S, Soler L, Hostettler A, Marescaux J, and Rémond Y (2012). Fast Segmentation of Abdominal Wall: Application to Sliding Effect Removal for Non-rigid Registration. *Abdominal Imaging;* pp. 198-207.

What is claimed is:

1. A method for real time laparoscopic navigation, the method comprising:
   scanning a structure of interest internal to a patient to provide a first set of image data via a scanner;
   generating a first three-dimensional reconstruction of the structure of interest based on the first set of image data;
   annotating the first three-dimensional reconstruction of the structure of interest with a plurality of reference points;
   obtaining spatial coordinates of the plurality of reference points during a laparoscopic procedure;
   providing a surgical port during the laparoscopic procedure, wherein:
      the surgical port comprises a proximal end located outside a body of the patient and a distal end located within an internal portion of the body of the patient;

the surgical port comprises a channel extending between the proximal end of the surgical port and the distal end of the surgical port; and coupling a camera to the proximal end of the surgical port, wherein the camera comprises a field of view directed away from the distal end of the surgical port and away from the body of the patient;

inserting a surgical tool into the body of the patient via the channel in the surgical port;

obtaining a second set of image data associated with a plurality of reference markers external to the body of the patient, wherein:
- the second set of image data is captured in the field of view of the camera;
- the plurality of reference markers are positioned on a ceiling of a room in which the surgical port is located; and determining, using the second set of image data associated with the plurality of reference markers, a global position of the surgical port and the surgical tool inserted into the surgical port; and generating a second three-dimensional reconstruction of the structure of interest based on the spatial coordinates, wherein:
- the first three-dimensional reconstruction of the structure of interest illustrates the structure of interest before articulation of a support surface;
- the obtaining the spatial coordinates of the plurality of reference points comprises obtaining a distance from each of the plurality of reference points to the camera; and
- the second three-dimensional reconstruction of the structure of interest is a tissue deformation simulation used to simulate changes in a shape of the structure of interest after the articulation of the support surface.

2. The method of claim 1 wherein the distance is obtained via a laser.

3. The method of claim 1 wherein the distance is obtained via acoustic waves.

4. The method of claim 1 wherein the distance is obtained via an autofocus feature of the camera.

5. The method of claim 4 wherein the autofocus feature incorporates an algorithm to increase local pixel contrast.

6. The method of claim 1 wherein the structure of interest is a liver.

7. The method of claim 6 wherein the plurality of reference points comprises locations where hepatic arteries enter the liver and where a portal vein exits the liver.

8. The method of claim 6 wherein the plurality of reference points comprises locations including a transverse fissure of the liver that divides a left portion of the liver into four segments.

9. The method of claim 6 wherein the plurality of reference points comprises a coupling point between the liver and a gallbladder.

10. The method of claim 6 wherein the plurality of reference points comprises a location of a hepatic lymph node.

11. The method of claim 6 wherein the plurality of reference points comprises a ligamentum venosum and a ligament teres.

12. A real time laparoscopic navigation system comprising:
- a scanner configured to provide a first set of image data of a structure of interest internal to a patient;
- a surgical port;
- a plurality of reference markers external to a body of the patient, wherein
  - the plurality of reference markers are positioned on a ceiling of a room in which the surgical port is located;
- a camera coupled to the surgical port, wherein:
  - the surgical port comprises a proximal end configured to be located outside the body of the patient and a distal end configured to be located within an internal portion of the body of the patient; and
  - the surgical port comprises a channel extending between the proximal end of the surgical port and the distal end of the surgical port;
  - the camera is coupled to the proximal end of the surgical port;
  - the camera comprises a field of view directed away from the distal end of the surgical port and away from the body of the patient;
  - the field of view is configured to capture a second set of image data associated with the plurality of reference markers;
- a surgical tool configured to be inserted into the body of the patient via the channel in the surgical port; and
- a processor configured to:
  - generate a first three-dimensional reconstruction of the structure of interest based on the first set of image data;
  - annotate the first three-dimensional reconstruction of the structure of interest with a plurality of reference points;
  - obtain spatial coordinates of the plurality of reference points during a laparoscopic procedure;
  - determine, using the second set of image data associated with the plurality of reference markers, a global position of the surgical port and the surgical tool inserted into the surgical port;
  - generate a second three-dimensional reconstruction of the structure of interest based on the spatial coordinates; and
  - obtain the spatial coordinates of the plurality of reference points during the laparoscopic procedure by obtaining a distance from each of the plurality of reference points to the camera, wherein:
    - the first three-dimensional reconstruction of the structure of interest illustrates the structure of interest before articulation of a support surface;
    - the second three-dimensional reconstruction of the structure of interest is a tissue deformation simulation used to simulate changes in a shape of the structure of interest after the articulation of the support surface.

13. The system of claim 12 wherein the scanner is a magnetic resonance imaging (MRI) scanner.

14. The system of claim 12 wherein the scanner is a computed tomography (CT) scanner.

15. The system of claim 12 wherein the processor is configured to obtain the distance via a laser.

16. The system of claim 12 wherein the processor is configured to obtain the distance via acoustic waves.

17. The system of claim 12 wherein the processor is configured to obtain the distance via an autofocus feature of the camera.

18. The system of claim 17 wherein the autofocus feature incorporates an algorithm to increase local pixel contrast.

* * * * *